(12) United States Patent
Arrivat et al.

(10) Patent No.: US 6,521,805 B2
(45) Date of Patent: Feb. 18, 2003

(54) ISOBUTENE POLYMERIZATION PROCESS

(75) Inventors: Eric Arrivat, Istres (FR); Gacam Benazzouz, Martigues (FR); Alain Pinede, Ventabren (FR); Christian Sait, Cornillon-Confoux (FR)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/984,878

(22) Filed: Oct. 31, 2001

(65) Prior Publication Data

US 2002/0065445 A1 May 30, 2002

Related U.S. Application Data

(63) Continuation of application No. PCT/GB00/02174, filed on Jun. 6, 2000.

(30) Foreign Application Priority Data

Jun. 11, 1999 (FR) .............................................. 99 07649

(51) Int. Cl.[7] .............................. C07C 2/04; C08F 2/00; C08F 10/10; C08F 110/10
(52) U.S. Cl. ........................ 585/502; 585/501; 526/59; 526/60; 526/61; 526/348.7
(58) Field of Search ................................. 585/501, 502; 526/59, 60, 61, 348.7

(56) References Cited

U.S. PATENT DOCUMENTS

| 4,469,853 A | * | 9/1984 | Mori | 526/59 |
| 4,620,049 A | | 10/1986 | Schmidt et al. | 585/501 |
| 5,116,915 A | * | 5/1992 | Mamedov et al. | 526/339 |
| 5,155,184 A | * | 10/1992 | Laurent et al. | 526/348.4 |

FOREIGN PATENT DOCUMENTS

| EP | 0 099 131 | 1/1984 |
| EP | 0 398 706 | 11/1990 |
| FR | 2 625 506 | 7/1989 |
| FR | 2 749 014 | 11/1997 |
| WO | 96/41822 | 12/1886 |

\* cited by examiner

*Primary Examiner*—Walter D. Griffin
(74) *Attorney, Agent, or Firm*—Nixon & Vanderhye

(57) ABSTRACT

Isobutene polymerization process wherein a property P (viscosity or average molecular weight) of the polyisobutene product is maintained constant. The polymerization is conducted continuously in a reactor comprising a boiling liquid reaction phase in equilibrium with a gas phase, by continuous introduction into the reactor of a catalyst and of a C4 hydrocarbon feed mixture comprising the monomer, and by continuous withdrawal from the reactor of the liquid reaction phase. The process comprises the determination of a target value V of the partial pressure, PiC4, of the isobutene in the reactor gas phase corresponding to the desired value of the property P, by virtue of an empirical relationship established beforehand between the property P of the polyisobutene product and PiC4. During the polymerization, PiC4 is measured and a corrected value of PiC4, (PiC4)$c$, is calculated and is held constant at around the target value V, by acting on the flow rate Qc of the catalyst and/or on the flow rate Qh of the C4 hydrocarbon feed mixture.

13 Claims, 15 Drawing Sheets

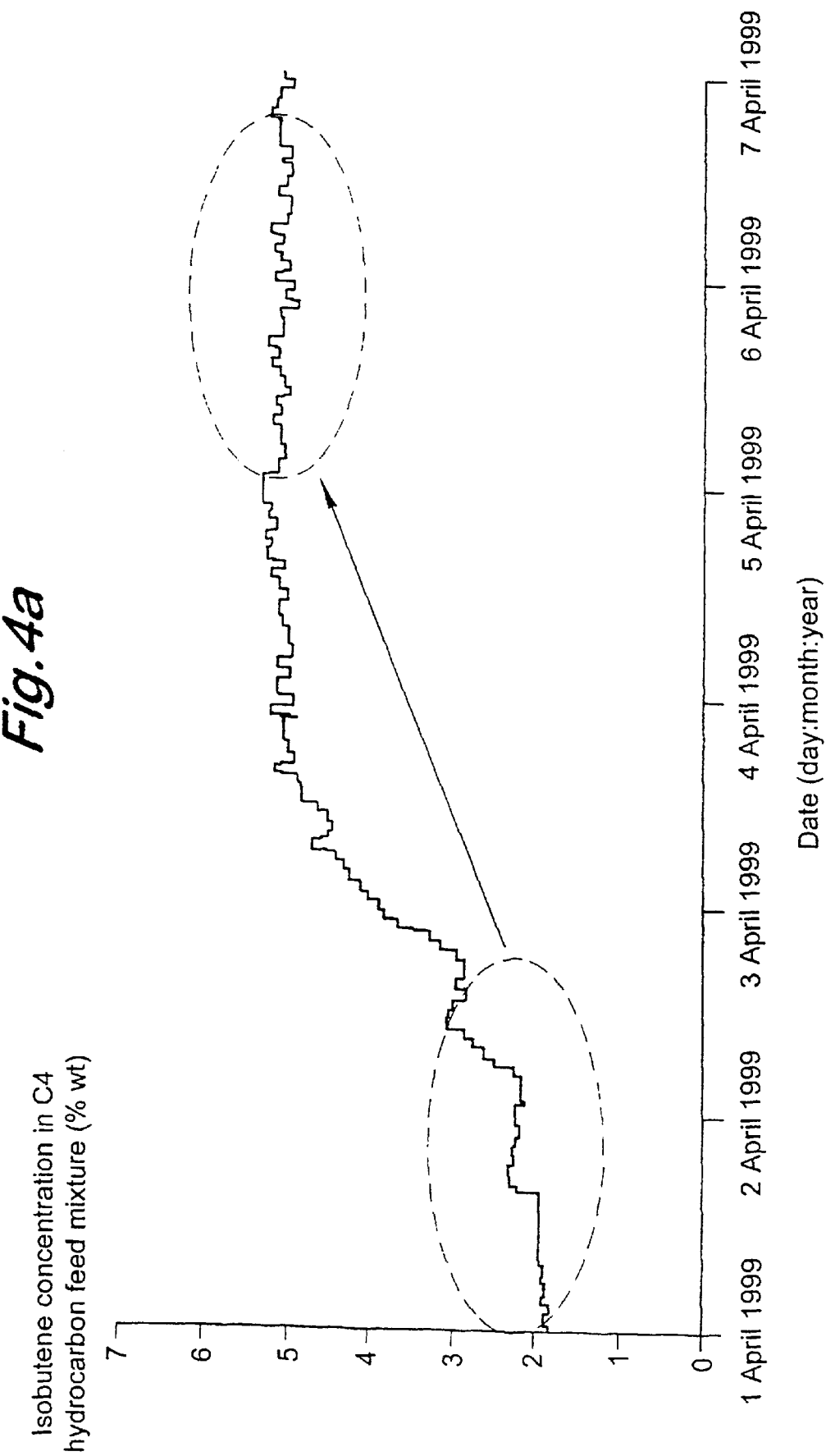

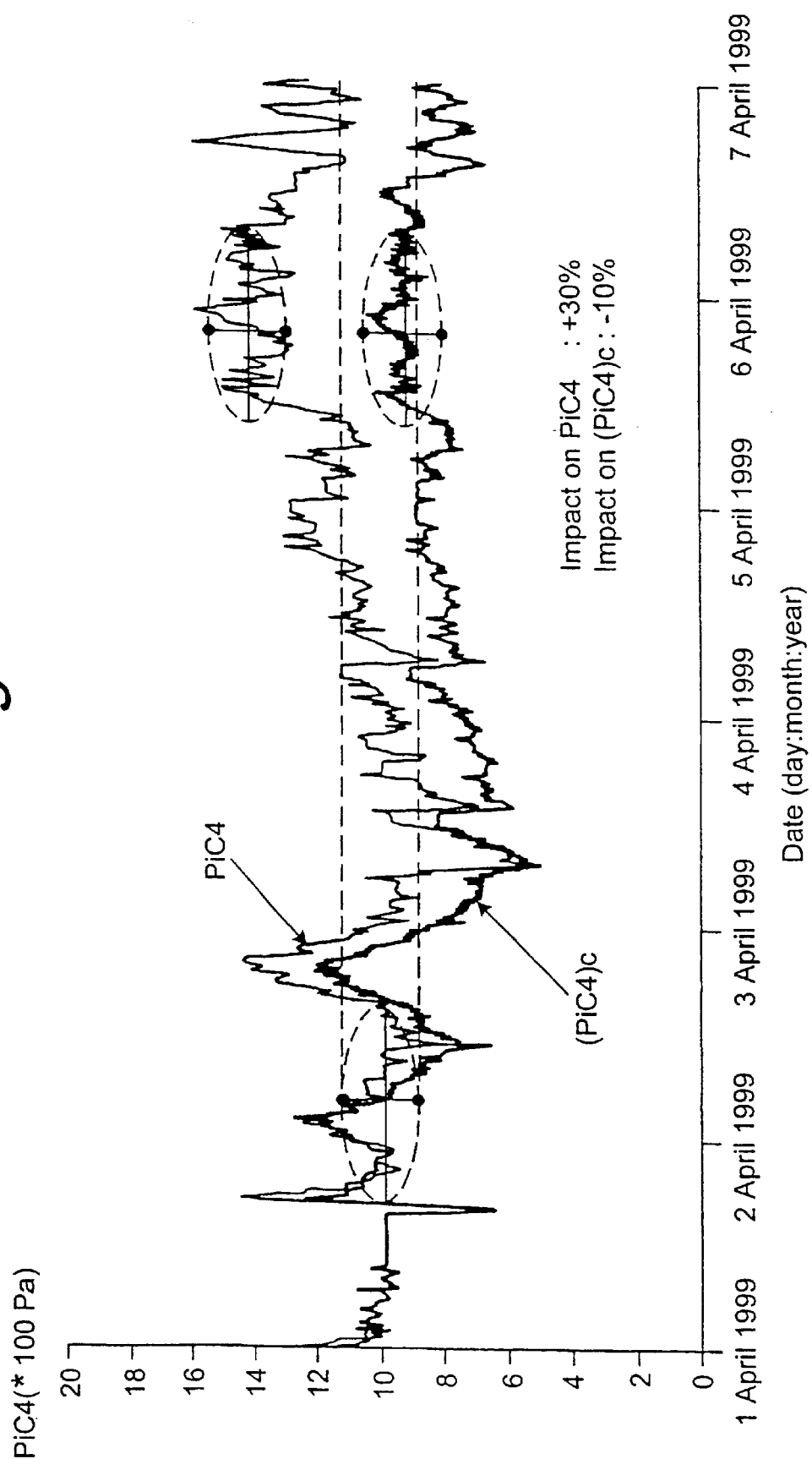

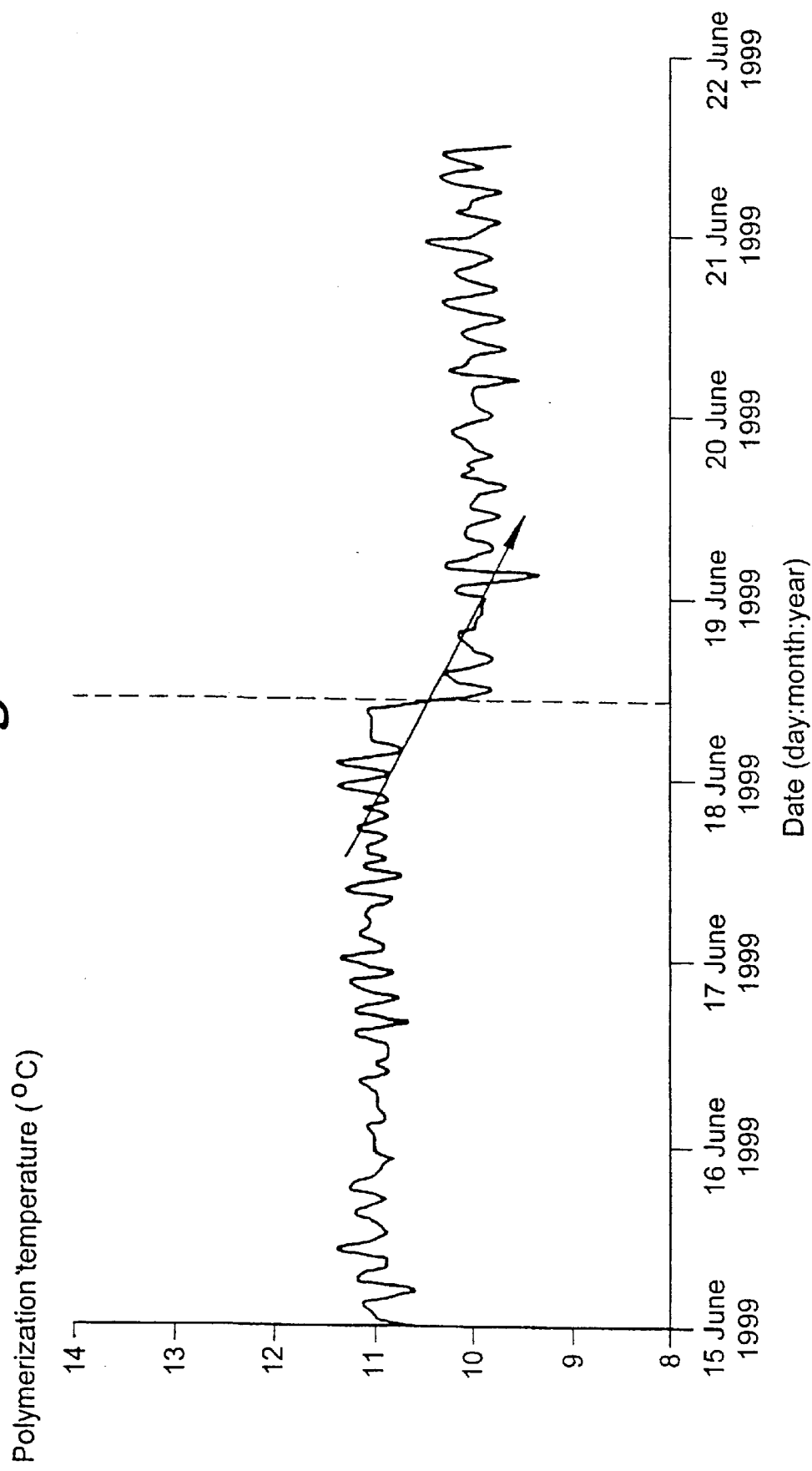

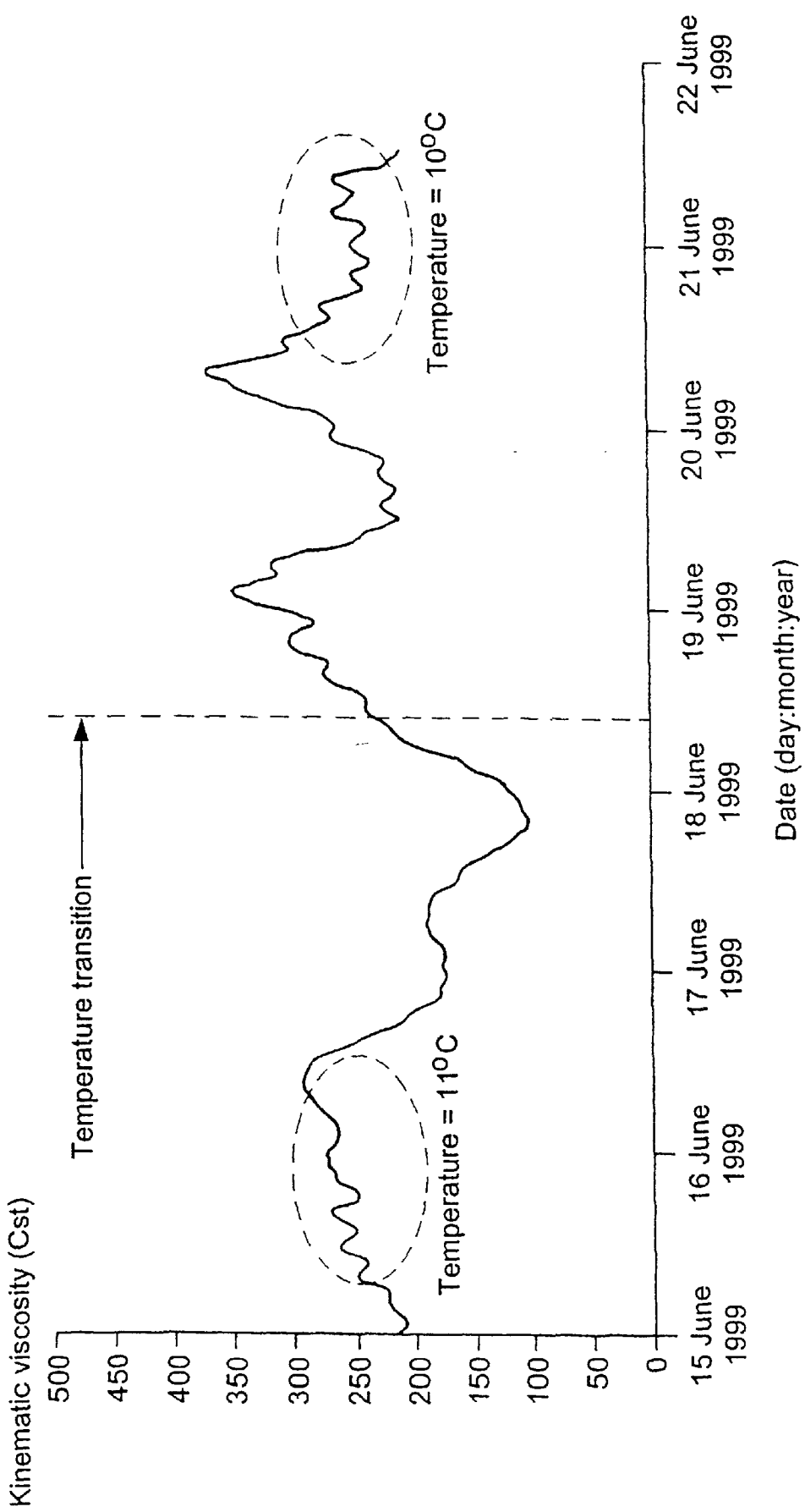

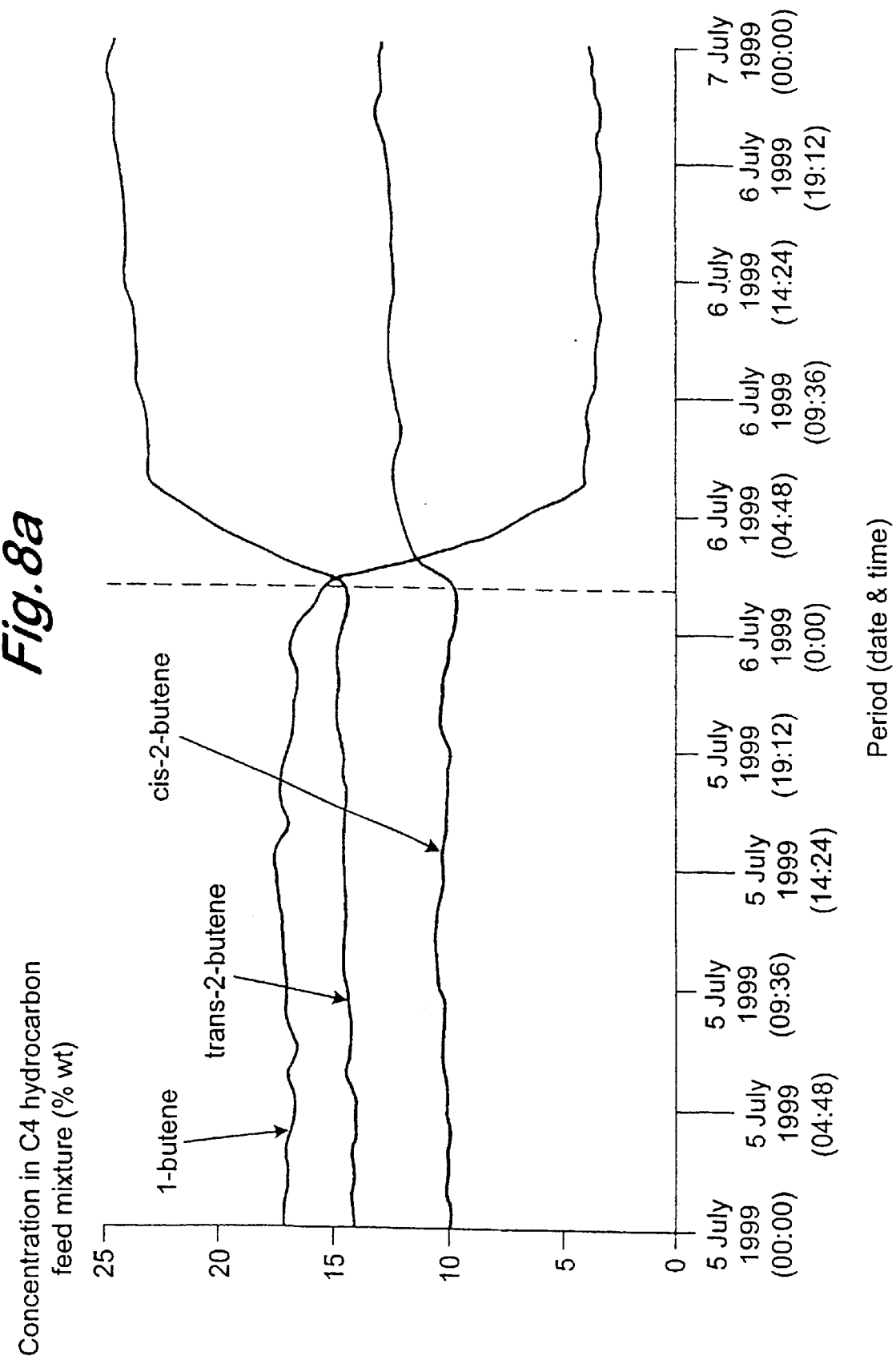

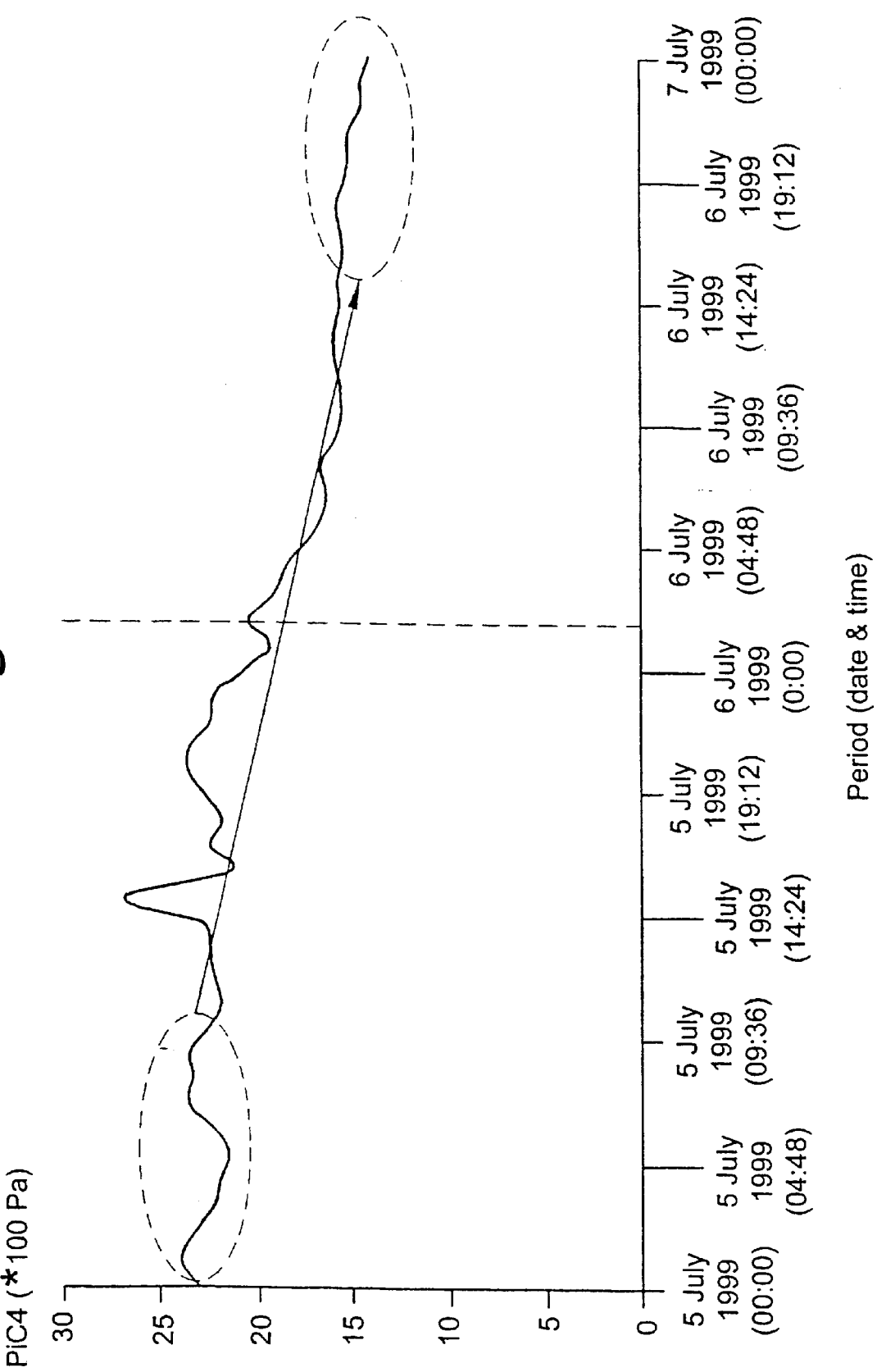

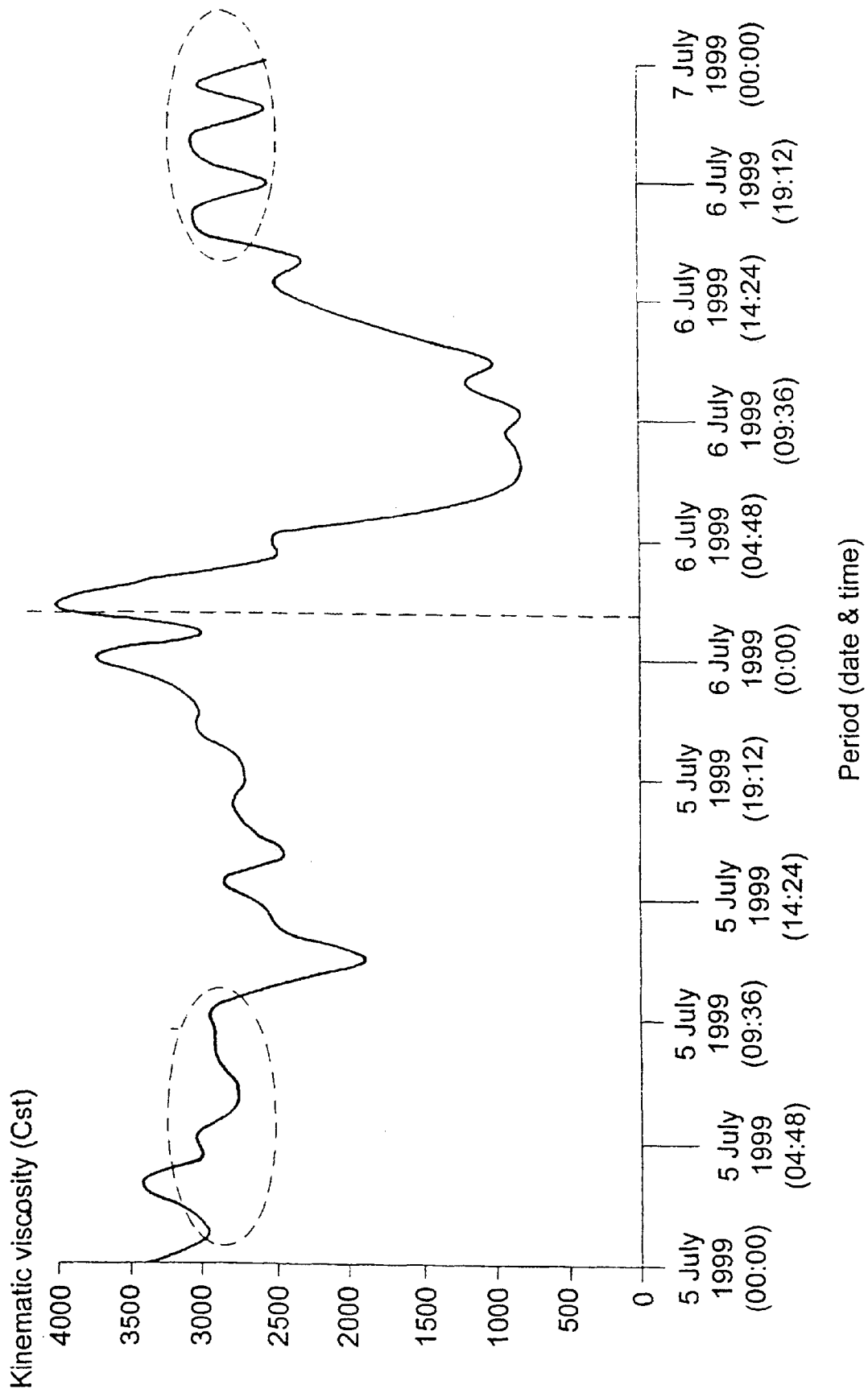

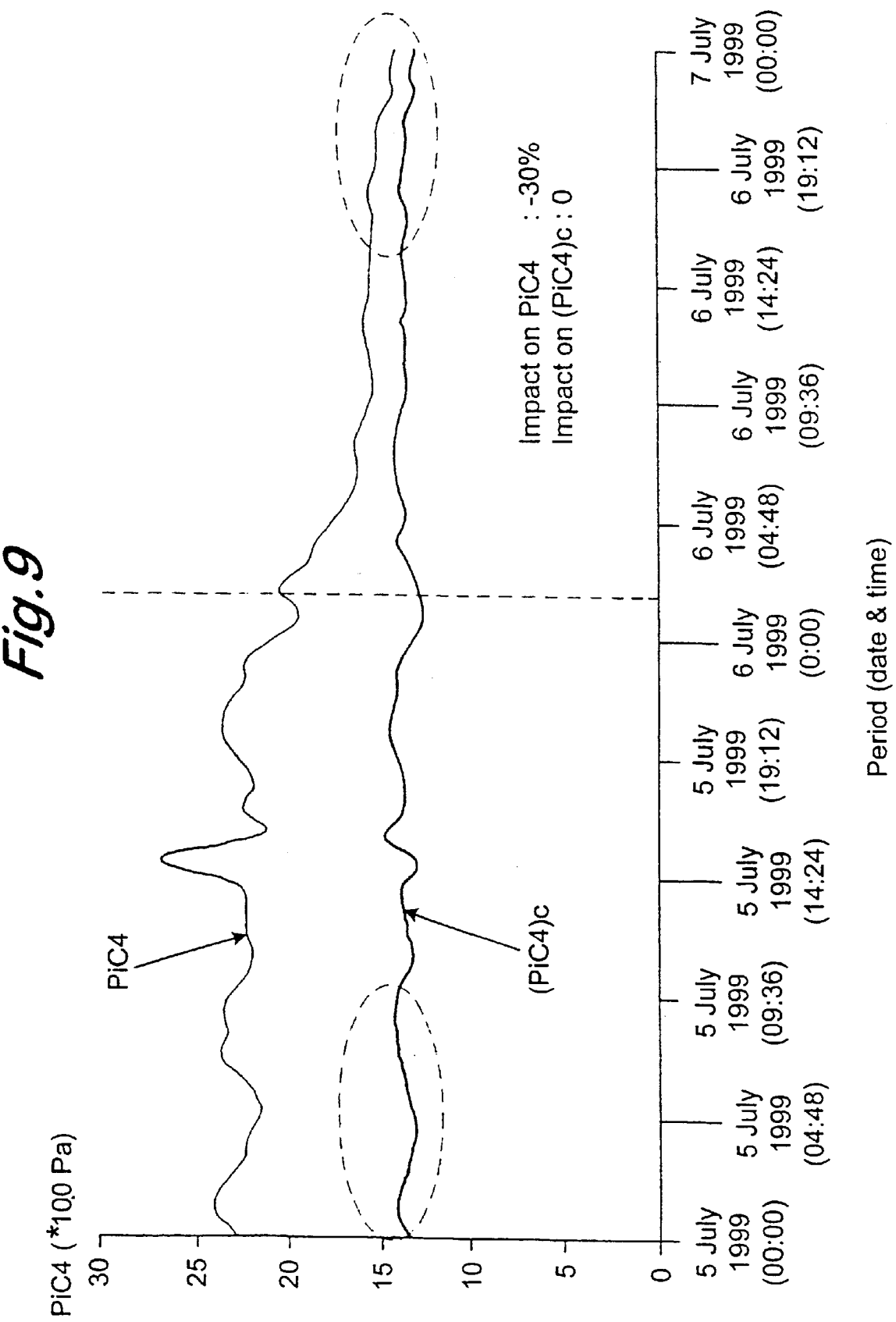

ISOBUTENE POLYMERIZATION PROCESS

The present application is a continuation of PCT/GB00/02174, filed Jun. 6, 2000.

BACKGROUND OF THE INVENTION AND SUMMARY OF THE INVENTION

The present invention relates to a process which makes it possible to control the viscosity or the average molecular mass of a polyisobutene produced continuously in a reactor in liquid phase.

It is known to polymerize isobutene continuously in a reactor comprising a boiling liquid reaction phase containing the monomer and the polymer being formed, above which there is a gas phase comprising, in particular, the monomer which is in equilibrium with the liquid phase. The continuous polymerization is brought about in particular by continuous feeds into the reactor of the monomer and of a catalyst and by continuous withdrawal from the reactor of the liquid phase, which is, generally, subjected subsequently to one or more purification steps which are intended to isolate the polyisobutene produced.

The monomer often consists of isobutene originating from a mixture of butenes and/or butanes.

In general, the polymerization reaction is conducted continuously with the aid of a catalyst of cationic type and, if appropriate, of a cocatalyst.

In a continuous polymerization, the monomer, i.e. isobutene, is generally supplied by means of an essentially C4 hydrocarbon cut; that is to say, a mixture comprising isobutene, other C4 olefins and/or C3 to C7 alkanes, especially C4 alkanes. The quality of the monomer supply may vary over time, such that it adversely affects the polymerization conditions and, consequently, the quality of the polymer obtained.

The applications of polyisobutenes are often linked to their rheological properties. One of the essential characteristics of polyisobutene is its viscosity or its average molecular mass.

In a continuous polyisobutene production process, the average residence time of the polymer in the polymerization reactor can be relatively long. Moreover, the reaction mixture withdrawn continuously from the polymerization reactor enters one or more polymer purification steps. The final polymer is therefore isolated and purified after an additional time which may generally be a number of hours, for example from 3 to 12 hours, such that any analysis of the polymer at the end of this last step is carried out very late. Consequently, the time elapsed between a deviation measurable from the analysis of the viscosity or of the average molecular mass of the polyisobutene, and the correction of the said-deviation in the polymerization reactor, is relatively great. This type of deviation therefore gives rise to the production of product which is outside the specifications of viscosity or average molecular mass, generally in a not inconsiderable amount.

Methods have been investigated in the past to partially solve the above mentioned problem.

In the process of the French Patent Application 2 625 506, a method is disclosed to determine one or more polymer properties using a correlative relation with absorption measurements carried out on the polymer with an infrared spectrophotometer. A process control using this method is also disclosed but it does not address the problem solved by the present invention.

The U.S. Pat. No. 4,620,049 describes a method adapted for controlling the molecular weight of a product output from a polybutene reactor. The method in particular comprises determining a formula correlating molecular weight simultaneously with temperature of the reactor and concentration of isobutene in the reactor. The desired product molecular weight is then obtained by altering, through the use of the formula, the temperature of the reactor and/or the concentration of isobutene in the reactor. However the principle of this method does not comprise maintaining constant a corrected value of the isobutene partial pressure in the reactor gas phase, in particular independently of the polymerization temperature. Moreover, involving the temperature of the reactor in the formula of this method implies that the temperature may vary even slightly and therefore affects the quality of polyisobutene produced, such as the unsaturated termination content of the polymer.

The technical problem to be solved is to find a process control which makes it possible to correct the fluctuations in viscosity or average molecular mass of the polyisobutene and thus to intervene more rapidly in the conditions of the polymerization in the reactor in order to limit the quantity of polyisobutene which is produced outside the specifications.

This problem was partially solved by the process described in French Patent Application Filing No. 9903267, which makes it possible to maintain a property P at a constant value, the property P being selected from the viscosity or the average molecular mass, firstly by determining a target value V for the isobutene partial pressure $PiC4$ in the gas phase of the reactor, which corresponds to the desired value of the property P, and secondly by maintaining the said partial pressure at a constant value around the target value V by acting on the flow rate Qc of the catalyst introduced into the reactor and/or on the flow rate Qh of the C4 hydrocarbon feed mixture.

The invention described in French Patent Application Filing No. 9903267 nevertheless presents possibilities for improvement. Indeed, despite the maintenance of the isobutene partial pressure $PiC4$ at a constant value it has been observed that the property P sometimes has a tendency to deviate. Consequently, it is often necessary to readjust the said partial pressure, which often results in the production of product which is outside the specification.

The process control based on maintaining the partial pressure $PiC4$ at a constant value was employed in the process of the patent application owing in particular to the difficulty of measuring the concentration of isobutene in the reactive liquid phase of the reactor. The partial pressure $PiC4$ can be considered as a weighted image of the concentration of isobutene in the reactive phase, in accordance with the laws of liquid/vapour equilibrium.

It has been found that various parameters acting on the reaction mixture are able to modify this liquid/vapour equilibrium and influence the partial pressure $PiC4$ without directly affecting the property P of the polyisobutene produced.

The task was therefore undertaken of improving the process by researching which were the determining parameters which influenced the liquid/vapour equilibrium, in order to correct the partial pressure $PiC4$ and so to avoid the undesirable effects referred to above. The partial pressure $PiC4$ value corrected in this way can become independent of the liquid/vapour equilibrium and can thus be used to control the property P with greater reliability.

The subject of the present invention therefore lies in a process which involves using new parameters in an improved control, and in particular lies in a modelling of the partial pressure PiC4 which thereby makes it possible in particular to improve the process described in French Patent Application Filing No. 9903267.

The present invention relates to a process for maintaining a property P of a polyisobutene at a constant desired value in the course of an isobutene polymerization conducted continuously in a reactor comprising a boiling liquid reaction phase which contains the monomer and the polymer being formed and is in equilibrium with a gas phase on top of the said liquid phase, the polymerization being conducted by continuous introduction into the reactor of a catalyst and of a C4 hydrocarbon feed mixture comprising the monomer, and by continuous withdrawal from the reactor of the liquid reaction phase, which is subsequently subjected continuously to at least one purification step which is intended to isolate the polyisobutene produced, this process being characterized in that the property P is selected from the viscosity and the average molecular mass of the polyisobutene produced and in that, by virtue of an empirical relationship established beforehand between the property P of the polyisobutene produced and the partial pressure PiC4 of the isobutene in the gas phase of the reactor, a target value V is determined for PiC4, corresponding to the desired value of the property P, and in that, during the polymerization, the partial pressure PiC4 in the gas phase of the reactor, and at least one of the parameters selected from the polymerization temperature and the concentration of at least one of the constituents of the C4 hydrocarbon feed mixture, are measured, a corrected value of the isobutene partial pressure, (PiC4)c, is calculated from the measured value of PiC4 and from that of at least one of the said parameters, and the said corrected value (PiC4)c is held constant at around the said target value V by acting on the flow rate Qc of the catalyst introduced into the reactor and/or on the flow rate Qh of the C4 hydrocarbon feed mixture introduced into the reactor.

BRIEF DESCRIPTION OF THE DRAWINGS

FIG. 5 represents a simulation showing on the same axis the measured and corrected value of the isobutene partial pressure for the same episode as previously, and shows the advantages of the present invention.

FIGS. 8.a, 8.b, 8.c show trends extracted from an episode of a polyisobutene production plant data illustrating the impact of a variation of composition of the C4 hydrocarbon feed mixture on the kinematic viscosity, when using a process control from the prior art.

FIG. 9 represents a simulation showing on the same axis the measured and corrected value of the isobutene partial pressure for the same episode as previously, and shows the advantages of the present invention.

DETAILED DESCRIPTION OF PREFERRED EMBODIMENTS

Figure 1:
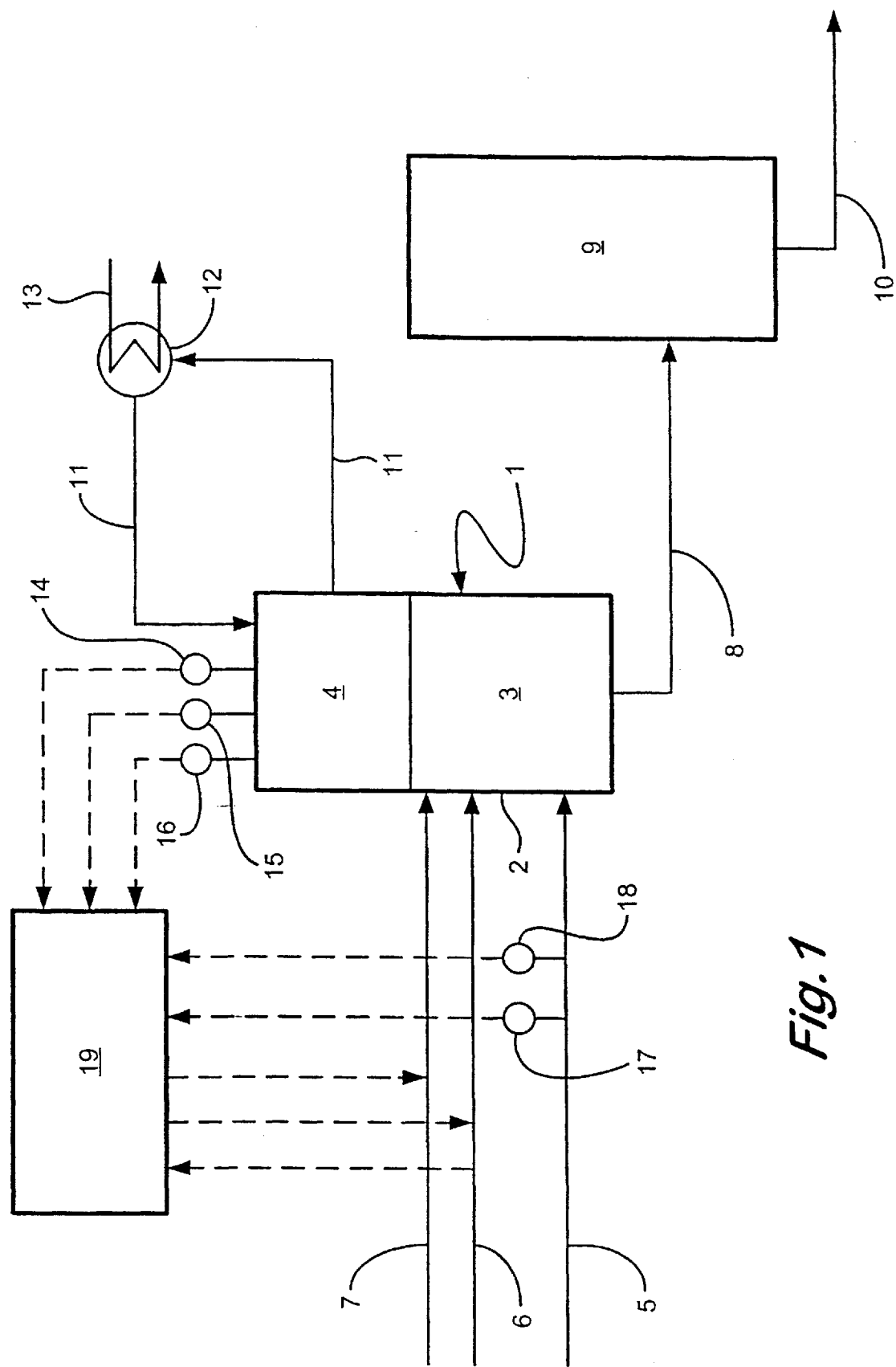
FIG. 1 shows, diagrammatically, an example of an apparatus for continuous production of the polyisobutene.

It has been found, surprisingly, that for a property P held constant it is possible to apply a correction to the isobutene partial pressure PiC4 such that the said corrected pressure is independent of any variation of the isobutene concentration CiC4 in the C4 hydrocarbon feed mixture, of the concentration of at least one of the compounds in the C4 hydrocarbon feed mixture, or of the polymerization temperature. Consequently, the isobutene partial pressure thus corrected, (PiC4)c is an essential and critical element in accordance with the present invention in the controlling of the viscosity or the average molecular mass of the polyisobutene produced continuously.

By concentration of at least one of the constituents of the C4 hydrocarbon feed mixture, it is generally meant concentration of at least one of the constituents in the said C4 hydrocarbon feed mixture. In a particular embodiment of the present invention this expression means concentration of at least one of the constituents in the liquid reaction phase or in the gas phase in equilibrium with said liquid reaction phase.

By property P is meant, generally, the viscosity or average molecular mass measured on the polyisobutene, especially after withdrawal of the liquid reaction phase from the reactor, and in particular after at least one step of purification intended to isolate the polymer produced.

According to one aspect of the present invention, the property P which will be held at a constant desired value during the polymerization can be any viscosity of the polyisobutene, selected, for example, from the kinematic viscosity, the dynamic viscosity, the specific viscosity, the reduced viscosity and the intrinsic viscosity. It is possible to measure the kinematic viscosity, i.e. the rate of flow of the polymer in a capillary tube, using, for example, the standardized method ASTM D445. It is also possible to measure the dynamic viscosity, which is linked to the kinematic viscosity by a relationship involving the density of the polymer, using, for example, a viscometer whose principle consists in measuring a pressure drop at a certain temperature and in calculating the viscosity from, for example, the Hagan-Poiseuille equation. More particularly, it is possible to use a viscometer under the trade name VISCOMATIC® produced by the company FLUIDYSTEME. It is also possible to measure the intrinsic viscosity in a solvent, for example cyclohexane, at a given temperature, for example 30° C.

The viscosity of the polyisobutene produced can also be measured by infrared or near-infrared spectrophotometry, such as is disclosed in French Patent Application No. 2 625 506.

The constant desired value of the viscosity of the polyisobutene produced can be that corresponding to:
  (i) a kinematic viscosity, measured at 100° C., of from 5 to 50,000 centiStocks (cSt), preferably from 10 to 40,000 cSt, or
  (ii) a dynamic viscosity, measured at 100° C., of from 4 to 45,000 centipoise (cP), preferably from 8 to 36,000 cP, or (iii) an intrinsic viscosity, calculated from the measurements of the specific viscosity of the polyisobutene in solution in cyclohexane at 30° C., of from 1 to 25 dl/g, preferably from 2 to 20 dl/g.

According to another aspect of the present invention, the property P which will be maintained at a constant desired value during the polymerization can be the average molecular mass of the polyisobutene produced. By average molecular mass is meant any average molecular mass of the polyisobutene, for example the number-average molecular mass, Mn, or weight-average molecular mass, Mw, which are generally measured by gel permeation chromatography, a method which is often known under the name of size exclusion chromatography, or else the viscometric average molecular mass, Mv. The average molecular mass of the polyisobutene produced can be measured by infrared or near-infrared spectrophotometry, such as is disclosed in French Patent Application No. 2 625 506.

The constant desired value of the average molecular mass of the polyisobutene produced can be that corresponding to:

(i) a number-average molecular mass, Mn, of from 300 to 6700 daltons, preferably from 400 to 6000 daltons, or (ii) a weight-average molecular mass, Mw, of from 400 to 20,000 daltons, preferably from 600 to 18,000 daltons, or (iii) a viscometric average molecular mass, Mv, of from 380 to 16,900 dl/g, preferably from 500 to 15,000 dl/g.

In the present invention, the polyisobutene can be an isobutene homopolymer or, more generally, a copolymer of isobutene with at least one other C4 olefin in a proportion of less than 30%, preferably of less than 25%, by weight, for example from 0.1 to 25% by weight. Generally speaking, high molecular weight polyisobutenes contain essentially isobutene. Low-viscosity polyisobutenes may comprise higher 1-butene and/or 2-butene comonomer contents than in high molecular weight polyisobutenes.

Thus, in the process of the present invention, the monomer consists of isobutene and the optional comonomers of 1-butene and cis- and trans-2-butene. The polymerization is conducted by continuous introduction into the reactor of a C4 hydrocarbon feed mixture comprising the monomer with generally at least one other C4 olefin and/or at least one C3 to C7 (cyclo)alkane, in particular a C4 alkane. Such a mixture may comprise by weight from 0 to 40%, preferably from 0 to 30%, of 1-butene, from 0 to 20%, preferably from 0 to 15%, of cis-2-butene, from 0 to 40%, preferably from 0 to 30%, of trans-2-butene, from 0 to 50%, preferably from 0 to 40%, of one or more C3 to C7 (cyclo)alkanes, such as butane or isobutane, and from 5 to less than 100%, preferably from 10 to less than 50%, of isobutene. In another embodiment of the present invention, the C4 hydrocarbon feed mixture introduced into the reactor may comprise, by weight, up to 99%, preferably up to 99.9%, especially up to 99.99% of isobutene.

The C4 hydrocarbon feed mixture can be introduced directly into the boiling liquid reaction phase. It can also be introduced indirectly into the boiling liquid reaction phase by addition to any other liquid introduced into the reactor, for example to a liquid obtained by cooling and condensation of condensable gas of the gas phase which escapes from the top part of the reactor and is returned into the reactor. The C4 hydrocarbon feed mixture can also be introduced in its entirety into the gas phase as a spraying liquid hydrocarbon, as disclosed in French Patent Application No. 2 749 014.

The boiling liquid reaction phase generally contains isobutene and one or more other C4 olefins and/or one or more C3 to C7 (cyclo)alkanes, the polymer being formed, the catalyst and, if appropriate, a cocatalyst.

The boiling liquid reaction phase can be agitated by any known means, in particular with the aid of a mechanical stirrer. The boiling liquid reaction phase can also be agitated by forced circulation of this medium, which can include the withdrawal and the reintroduction into the reactor of a portion of the boiling liquid reaction phase, in particular with the aid of a so-called recycling pump.

The boiling liquid reaction phase has above it a gas phase, especially a condensable gas phase Consequently, a condensable gas can escape from the top part of the reactor containing the gas phase In general, this gas is condensed outside the reactor in order, in particular, to remove the heat from the polymerization reaction. After cooling and condensation of this gas, a cooled liquid is recovered which can be recycled to the gas phase and/or to the boiling liquid reaction phase. Some or all of the C4 hydrocarbon feed mixture can be added to this liquid.

In order to carry out the polymerization of the isobutene, a catalyst is used which is generally suitable for cationic olefin polymerization, often called a catalyst of cationic type, in the presence, if appropriate, of a cocatalyst. More particularly, the catalyst can be a halogenated boron compound such as boron trifluoride, or an organoaluminium compound, for example of formula AlRnXn–3 in which R is an alkyl radical having, for example, from 1 to 10 carbon atoms, X is a chlorine or bromine atom and n is an integral or fractional number ranging from 0 to 3. The cocatalyst can be water, hydrochloric acid, an alkyl halide such as tert-butyl chloride, or else an alcohol, such as ethanol, especially when boron trifluoride is used as catalyst.

The polymerization reaction can in particular be carried out using an alkyl halide such as tert-butyl chloride as cocatalyst by the process disclosed in European Patent Application EP-A-0 645 402, in combination with ethyldichloroaluminium as catalyst.

The molar ratio of the amount of cocatalyst to the amount of catalyst which are introduced into the reactor is advantageously held at a constant value over time and is between 0.05 and 20, preferably between 1 and 10.

The catalyst and the cocatalyst are preferably introduced into the reactor separately from one another. One of them can be introduced in the C4 hydrocarbon feed mixture. Some or all of the cocatalyst or of the catalyst can be introduced into the reactor in a mixture with another liquid, for example with a portion of the boiling liquid reaction phase which is withdrawn and recycled, which makes it possible to ensure agitation of the reaction medium.

The polymerization reaction can be carried out at a temperature of between –30 and +50° C., preferably between –20 and +25° C. The polymerization temperature may be measured in the liquid reaction phase or in the gas phase in equilibrium with said liquid reaction phase. The polymerization temperature is preferably measured in the liquid reaction phase. The absolute pressure of the reactor is a function of the polymerization temperature and can range from 0.03 to 1, preferably from 0.05 to 0.5, MPa. The partial pressure PiC4 of the isobutene in the gas phase of the reactor can be greater than or equal to $1 \cdot 10^{-4}$ and less than 1 MPa, preferably greater than or equal to $3 \cdot 10^{-4}$ and less than 0.5 MPa.

The polymerization temperature is preferably held constant by acting on a cooling fluid of the reactor or of a condenser which is positioned on a line for recycling the gas phase which escapes from the top part of the reactor. Maintaining the polymerization temperature constant allows to obtain a product output with a steady concentration of unsaturated terminations.

The process according to the present invention may also comprise a centralized control unit which makes it possible to control the various polymerization parameters, such as the polymerization temperature, the total pressure and the partial pressures in the gas phase of the reactor, the concentration of the various products in the boiling liquid reaction phase, the rates of introduction of the various feeds of the reactor and of withdrawal from the boiling liquid reaction phase, and also the quality of the polyisobutene produced. This centralized control unit may comprise calculation modules and also regulators. A regulator is defined as a system enabling a measured value to be compared with a target value while acting on a physical parameter which makes it possible to change over time the said measured value so as to approach the said target value, taking into account the difference between these two values. The principal inputs of a regulator can therefore be distinguished as being the measured value of the physical parameter and the set point of the said parameter, which can be entered directly into the regulator as a target value by an operator or else displayed as a result of a calculation carried out by a calculation module.

The various process control operations carried out by a centralized control unit, in particular by a regulator, can be carried out directly by an operator.

According to the invention, the isobutene partial pressure PiC4 can be the result of a calculation based on the mass concentration of isobutene in the gas phase of the reactor and on the relative or absolute total pressure of the reactor, in particular the product of the absolute or relative total pressure of the reactor with the mass concentration of isobutene in the gas phase. The measured value M of the isobutene partial pressure PiC4 is commonly understood to mean the result of the abovementioned calculation, carried out on the basis of the values measured for the relative or absolute total pressure of the reactor and for the mass concentration of isobutene in the gas phase, carried out for example with the aid of a gas chromatograph. In the same way, the action which consists in measuring the isobutene partial pressure PiC4 commonly amounts to measuring the two above values and in carrying out the above calculation.

The total pressure in the reactor is generally not held constant and vary according to disturbances such as the quality of the C4 hydrocarbon feed mixture and/or the height of the boiling liquid reaction phase in the reactor.

According to the invention, a target value V is determined for the partial pressure PiC4 of the isobutene in the gas phase of the reactor corresponding to the desired value of the property P. To do this, an empirical relationship established beforehand between the property P of the polyisobutene produced and the isobutene partial pressure PiC4 in the gas phase of the reactor is used. In practice, the empirical relationship is established by means of series of prior measurements of the property P and of PiC4 under polymerization conditions in the reactor. This empirical relationship can be shown in the form of a table in which each value for viscosity or for average molecular mass of the polyisobutene produced is correlated with the isobutene partial pressure in the gas phase of the reactor.

One of the difficulties which the present invention aims to resolve results precisely from the fact that this empirical relationship remains heavily dependent on other parameters which are not easily controlled during the polymerization, such as the polymerization temperature or the quality of the C4 hydrocarbon feed mixture.

The target value V for the isobutene partial pressure in the gas phase of the reactor can be determined using the empirical relationships set out above, on the basis of a desired value for the property P of the polyisobutene produced and various settings of the physical parameters of the polymerization, such as the catalyst flow rate, cocatalyst flow rate, 1-butene concentration and cis- and/or trans-2-butene concentration. It is also possible to enter the desired value for the property P directly into a calculation module which comprises a model consisting of one or more empirical relationships set out above and which calculates the target value V for the isobutene partial pressure in the gas phase of the reactor.

One preferred embodiment of the present invention consists in modelling the partial pressure PiC4 as a function of the concentration (for example, the concentration by mass) of isobutene, CiC4, in the C4 hydrocarbon feed mixture, of a function F1 of the concentration (for example, concentration by mass) of at least one compound in the same hydrocarbon mixture, of a function F2 of the polymerization temperature, of a function of the rate of conversion of the isobutene to polymer, and in that:

1) the concentration (for example, concentration by mass) of isobutene, CiC4, in the C4 hydrocarbon feed mixture, the concentration (for example, concentration by mass) of the compound (or compounds) in the same hydrocarbon mixture in the function F1, the polymerization temperature and the partial pressure PiC4 are measured,
2) from the second and third measurements of the preceding stage, the functions F1 and F2 are calculated,
3) from F1, F2, CiC4 and the partial pressure measurement PiC4, a corrected partial pressure of PiC4, namely (PiC4)c, is calculated which is independent of any variations of CiC4, of the concentration (for example concentration by mass) of the compound (or compounds) in the C4 hydrocarbon feed mixture in the function F1, or of the polymerization temperature,
4) the corrected partial pressure (PiC4)c is held constant at around the target value, V, of PiC4 by acting on the flow rate Qc of the catalyst introduced into the reactor and/or on the flow rate Qh of the C4 hydrocarbon feed mixture introduced into the reactor.

According to the invention, the isobutene partial pressure PiC4 can be modelled as a function of the concentration (for example, concentration by mass) of isobutene, CiC4, in the C4 hydrocarbon feed mixture, of a function F1 of the concentration (for example, concentration by mass) of at least one compound in the same hydrocarbon mixture, of a function F2 of the polymerization temperature, of a function of the rate of conversion of the isobutene to polymer. According to the law of liquid/vapour equilibrium, the isobutene partial pressure PiC4 can be calculated by a product of the concentration by mass of the isobutene in the liquid phase of the reactor, $CiC4_{R2}$, and of the liquid/vapour equilibrium coefficient $k_H$.

The concentration by mass of the isobutene in the liquid phase of the reactor, $CiC4_{R2}$, depends essentially on the rate of conversion of the isobutene to polymer, Conv, which is the ratio between the mass of isobutene consumed by the polymerization reaction per unit time and the mass of isobutene introduced into the reactor by the C4 hydrocarbon feed mixture during the same unit of time. By means of a mass balance on the reactor, the following is written:

$$Conv = 1 - \frac{R3 * CiC4_{R3} + R2 * CiC4_{R2}}{Qh * CiC4} \quad (1)$$

where:

Qh: Mass flow rate of the C4 hydrocarbon feed mixture.
R2: Mass flow rate of the polyisobutene used.
R3: Mass flow rate of the gas phase of the reactor, which is recycled after cooling and condensation.
CiC4: Mass concentration of the isobutene in the C4 hydrocarbon feed mixture.
$CiC4_{R2}$: Mass concentration of the isobutene in the liquid phase of the reactor.
$CiC4_{R3}$: Mass concentration of the isobutene in the gas phase of the reactor, which is recycled after cooling and condensation.
Conv: Rate of conversion of the isobutene to polymer.

From this, the following is deduced:

$$CiC4_{R2} = \frac{(1-Conv)*Qh*CiC4}{R2} - \frac{R3*CiC4_{R3}}{R2} \quad (2)$$

The hypothesis is made that the final term in the preceding equation is negligible, and the following is written:

$$CiC4_{R2} = \frac{(1-Conv)*Qh*CiC4}{R2}$$

Since the concentration by mass $CiC4_{R2}$ is difficult to measure, a rate of conversion Conv' is defined by reference to the gas phase of the reactor, in accordance with the formula:

$$Conv' = 1 - \frac{R3*CiC4_{R3}}{Qh*CiC4} \quad (4)$$

The hypothesis is made that the rate of conversion Conv is proportional to the rate of conversion relative to the gas phase of the reactor, Conv', and the following is written:

$$Conv = a*Conv'$$

where a is a constant.

The concentration by mass of the isobutene, $CiC4_{R2}$, in the liquid phase of the reactor is therefore deduced from this:

$$CiC4_{R2} = \frac{Qh}{R2}*(1 - a*conv')*CiC4 \quad (6)$$

The liquid/vapour equilibrium coefficient $k_H$ depends essentially on the composition of the C4 hydrocarbon feed mixture and on the polymerization temperature (the pressure being equal to the equilibrium pressure). The model selected for the liquid/vapour equilibrium coefficient $k_H$ is a product of a function F1 of the concentration (for example, concentration by mass) of at least one of the compounds in the C4 hydrocarbon feed mixture and of a function F2 of the polymerization temperature. The following is written $$k_H = k_{H0}*F1*F2 \quad (7)$$

where $k_{H0}$ is a constant.

Using equations (6) and (7), a model of the partial pressure PiC4 is obtained, (PiC4)m, as a function of the concentration (for example, concentration by mass) of isobutene in the C4 hydrocarbon feed mixture, of a function F1 of the concentration (for example, concentration by mass) of at least one of the compounds in the same C4 hydrocarbon feed mixture, of a function F2 of the polymerization temperature and of a function of the rate of conversion of the isobutene:

$$(PiC4)m = k_{H0}*\frac{Qh}{R2}*CiC4*F1*F2(1-a*conv') \quad (8)$$

The compound (or compounds) of the function F1 can be selected from olefins such as isobutene, 1-butene, cis-2-butene and trans-2-butene and at least one C3 to C7 alkane and/or (cyclo)alkane, in particular a C4 alkane such as butane and/or isobutane.

The function F1 can be expressed in the form of a sum of linear functions of the concentration (for example, concentration by mass) of the compounds in the C4 hydrocarbon feed mixture centered around the averages of the said concentrations. F1 can thus be written as follows:

$$F1 = 1 + \Sigma ki*(Ci - Ci_{av}) \quad (9)$$

where:
Ci: concentration by mass of the compound i
ki, $Ci_{av}$: constants

This approximation is valid in so far as the variations in composition of the C4 hydrocarbon feed mixture are small.

The function F2 of the polymerization temperature can take the following form:

$$F2 = 1 + A*T^B \quad (10)$$

where:
T: polymerization temperature
A, B: constants

According to one of the aspects of the present invention, the concentration (for example, concentration by mass) of isobutene, CiC4, in the C4 hydrocarbon feed mixture, the concentration (for example, concentration by mass) of the compound (or compounds) in the same hydrocarbon mixture in the function F1, the polymerization temperature and the partial pressure PiC4 can be measured. The measurement of the concentration (for example, concentration by mass) of isobutene and of the compounds in the function F1 in the C4 hydrocarbon feed mixture is carried out, for example, with the aid of a gas chromatography apparatus. The polymerization temperature can be measured by any known method.

The functions F1 and F2 can be established on the basis of the concentration (for example, concentration by mass) of the compound (or compounds) in the same C4 hydrocarbon feed mixture and on the basis of the polymerization temperature. This operation can be carried out periodically by a calculation module.

According to the present invention, it is possible to calculate a corrected partial pressure PiC4, namely (PiC4)c, from F1, F2, CiC4 and the partial pressure measurement PiC4, such that the said corrected value (PiC4)c is independent of any variations of CiC4, of the concentration (for example, concentration by mass) of the compound (or compounds) in the C4 hydrocarbon feed mixture in the function F1, or of the polymerization temperature.

The corrected partial pressure (PiC4)c can be obtained
i) by specifying that the expression of the model of the isobutene partial pressure in the gas phase of the reactor in equation (8) (PiC4)m, is equal to the same measured partial pressure PiC4, namely $$(PiC4)m = PiC4, \quad (11)$$

ii) by specifying that the corrected partial pressure (PiC4)c is an independent function of the parameters influencing the liquid/vapour equilibrium, that is to say the term $$\frac{Qh}{R2} * (1 - a * conv'),$$

that is to say $$(PiC4)c = \frac{Qh}{R2} * (1 - a * conv'), \quad (12)$$

iii) and, on the basis of equations (8), (11) and (12), by writing the corrected partial pressure (PiC4)c in the form:

$$(PiC4)c = \frac{PiC4}{k_{HO} * CiC4 * F1 * F2} \quad (13)$$

The corrected partial pressure (PiC4)c can be calculated periodically by a calculation module. It may be judicious to adjust this expression regularly in order to avoid major deviations of the property P owing to the hypotheses made in the modelling of the isobutene partial pressure PiC4. In order to do this, two constants K1 and K2 are introduced, which are recalculated at regular intervals. The form of the equation for calculating the corrected partial pressure (PiC4)c may therefore be written:

$$(PiC4)c = K1 * \frac{PiC4 - K2}{K_{HO} * CiC4 * F1 * F2} \quad (14)$$

According to one aspect of the present invention, the corrected partial pressure (PiC4) is held constant around a target value V by acting on the flow rate Qc of the catalyst introduced into the reactor. The calculated value for the corrected partial pressure (PiC4)c can be compared with the target value V and the difference E=V−(PiC4)c between these two values can be calculated. As a function of the difference E, it is possible to act on the flow rate Qc of catalyst introduced in order to shift the isobutene partial pressure in the gas phase of the reactor towards the target value V. If the difference E is negative or less than the negative limit of a predetermined range centered around 0, the flow rate Qc of catalyst can be increased. If the difference E is positive or greater than the positive limit of the said range, the flow rate Qc of catalyst can be reduced. If the difference E is zero or is between the limits of the said range, the flow rate Qc of catalyst can remain unchanged. This type of process control can advantageously be implemented by the use of a regulator.

According to another aspect of the present invention, the corrected partial pressure (PiC4)c is held constant around a target value V by acting on the flow rate Qh of the C4 hydrocarbon feed mixture introduced into the reactor. In this case, the actions on the flow rate Qh are made relative to the difference E in a manner which is exactly the opposite of those described above on the flow rate Qc: therefore, instead of increasing the flow rate Qh, it is reduced, and vice versa.

The process of the present invention consists in particular in the modelling of the isobutene partial pressure in the gas phase of the reactor. It is possible, however, on the basis of this concept, to propose other variants of the process control claimed.

It is possible, for example, to propose a process in which a modelled value of PiC4 is calculated from parameters influencing the liquid vapour equilibrium, as they are defined in the invention, to give a desired value of PiC4, which is input as the set point of a regulator for maintaining the partial pressure PiC4 at around the desired value by acting on the flow rate Qc of the catalyst introduced into the reactor and/or on the flow rate Qh of the C4 hydrocarbon feed mixture introduced into the reactor.

A simplified form of the process may consist in displaying the target value V as the set point C of a regulator of the corrected partial pressure (PiC4)c of isobutene. In this case, the process can comprise the following steps:

(a) an empirical relationship is determined between the isobutene partial pressure in the gas phase of the reactor and the property P, the desired value of the property P is selected, and the target value V of the isobutene partial pressure in the gas phase of the reactor, corresponding to the desired value of the property P, is calculated with the said empirical relationship;

(b) the target value V calculated in (a) is displayed as the set point of a regulator of the corrected isobutene partial pressure;

(c) the concentration (for example, concentration by mass) of isobutene, CiC4, in the C4 hydrocarbon feed mixture, the concentration (for example, concentration by mass) of the compound (or compounds) in the same hydrocarbon mixture in the function F1, the polymerization temperature and the partial pressure PiC4 are measured;

(d) from the second and third measurements of the preceding step, the functions F1 and F2 are calculated;

(e) from F1, F2, CiC4 and the partial pressure measurement PiC4, a corrected partial pressure of PiC4, namely (PiC4)c, is calculated which is independent of any variations of CiC4, of the concentration (for example, concentration by mass) of the compound (or compounds) in the C4 hydrocarbon feed mixture in the function F1, or of the polymerization temperature;

(f) the regulator compares a corrected value for the isobutene partial pressure (PiC4)c with the target value V calculated in (a) and calculates the difference E=V−(PiC4)c between these two values;

(g) as a function of the difference E calculated in (f), the regulator acts on the flow rates Qc and/or Qh so as to shift the isobutene partial pressure in the gas phase of the reactor towards the target value V. In particular, if the regulator acts on the flow rate Qc, alternatively the difference E is negative or less than the negative limit of a predetermined range centered around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of being increased, and vice versa.

An elaborated form of the process can consist in displaying, as the set point C of a regulator of the corrected partial pressure (PiC4)c of isobutene, the result of a calculation whose result tends towards the target value V by an iterative variation as a function of time For example, the iterative variation, as a function of time, of the set point C towards the target value V can be a linear variation over time at a predetermined rate which can vary from 100 to 2000 Pa/h, preferably from 300 to 1500 Pa/h. In this case, the process can comprise the following steps:

(a) an empirical relationship is determined between the isobutene partial pressure in the gas phase of the reactor and the property P, the desired value of the property P is selected, and the target value V of the isobutene partial pressure in the gas phase of the reactor, corresponding to the desired value of the property P, is calculated with the said empirical relationship;

(b) the value to be displayed as set point C of a regulator of the corrected isobutene partial pressure, in order to reach the target value V calculated in step (a), is calculated by varying the said set point C iteratively over time with, for example, a linear variation, as a function of time, at a predetermined rate which can vary from 100 to 2000 Pa/h, preferably from 300 to 1500 Pa/h, (c) the concentration (for example, concentration by mass) of isobutene, CiC4, in the C4 hydrocarbon feed mixture, the concentration (for example, concentration by mass) of the compound (or compounds) in the same hydrocarbon mixture in the function F1, the polymerization temperature and the partial pressure PiC4 are measured;

(d) from the second and third measurements of the preceding step, the functions F1 and F2 are calculated;

(e) from F1, F2, CiC4 and the partial pressure measurement PiC4, a corrected partial pressure of PiC4, namely (PiC4)c, is calculated which is independent of any variations of CiC4, of the concentration (for example, concentration by mass) of the compound (or compounds) in the C4 hydrocarbon feed mixture in the function F1, or of the polymerization temperature;

(f) the regulator compares a corrected value for the isobutene partial pressure (PiC4)c with the set point C of the regulator calculated in (b) and calculates the difference E=C−(PiC4)c between these two values;

(g) as a function of the difference E calculated in (f), the regulator acts on the flow rates Qc and/or Qh so as to shift the isobutene partial pressure in the gas phase of the reactor towards the set point C. In particular, if the regulator acts on the flow rate Qc, alternatively the difference E is negative or less than the negative limit of a predetermined range centered around zero, in which case the flow rate Qc of catalyst is increased; or the difference E is positive or greater than the positive limit of the said range, in which case the flow rate Qc of catalyst is reduced, or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of being increased, and vice versa.

A more elaborated form of the process may also consist in limiting the actions of the regulator of the corrected partial pressure (PiC4)c, such that the regulator enters into action only when the measurement of the said isobutene partial pressure is outside a predetermined range around the target value V. The range can be not more than ±20%, preferably not more than ±10%, around the target value V. In this case, the process can comprise the following steps:

(a) an empirical relationship is determined between the isobutene partial pressure in the gas phase of the reactor and the property P, the desired value of the property P is selected, and the target value V of the isobutene partial pressure in the gas phase of the reactor, corresponding to the desired value of the property P, is calculated with the said empirical relationship;

(b) the target value V calculated in (a) is displayed as set point C of a regulator of the corrected isobutene partial pressure;

(c) the limits of a range of values for the isobutene partial pressure in the gas phase of the reactor are determined around the target value V, it being possible for the said limits to be not more than ±0%, preferably not more than ±10%, around the target value V;

(d) the concentration (for example, concentration by mass) of isobutene, CiC4, in the C4 hydrocarbon feed mixture, the concentration (for example, concentration by mass) of the compound (or compounds) in the same hydrocarbon mixture in the function F1, the polymerization temperature and the partial pressure PiC4 are measured;

(e) from the second and third measurements of the preceding step, the functions F1 and F2 are calculated;

(f) from F1, F2, CiC4 and the partial pressure measurement PiC4, a corrected partial pressure of PiC4, namely (PiC4)c, is calculated which is independent of any variations of CiC4, of the concentration (for example, concentration by mass) of the compound (or compounds) in the C4 hydrocarbon feed mixture in the function F1, or of the polymerization temperature;

(g) the regulator compares a corrected value for the isobutene partial pressure (PiC4)c with the said limits of the range as determined in (c), (h) if the corrected value (PiC4)c for the isobutene partial pressure is within the limits of the range as determined in (c), the regulator is deactivated and the flow rates Qc and/or Qh remain unchanged, (i) if the corrected value (PiC4)c for the isobutene partial pressure is outside the limits of the range as determined in (c):

(i) the regulator compares the corrected value (PiC4)c for the isobutene partial pressure in the gas phase of the reactor with the set point C of the regulator, and calculates the difference E=C−(PiC4)c between these two values;

(ii) as a function of the difference E, the regulator acts on the flow rates Qc and/or Qh so as to shift the corrected isobutene partial pressure (PiC4)c towards the set point C. In particular, if the regulator acts on the flow rate Qc, either the difference E is negative or less than the negative limit of a predetermined range centered around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of being increased, and vice versa.

Another more elaborated form of the process is able to combine the improvements set out in the two preceding paragraphs. In this case, the process can comprise the following steps:

(a) an empirical relationship is determined between the isobutene partial pressure in the gas phase of the reactor and the property P, the desired value of the property P is selected, and the target value V of the isobutene partial pressure in the gas phase of the reactor, corresponding to the desired value of the property P, is calculated with the said empirical relationship;

(b) the limits of a range of values for the corrected isobutene partial pressure (PiC4)c are determined around the target value V;

(c) the concentration (for example, concentration by mass) of isobutene, CiC4, in the C4 hydrocarbon feed mixture, the concentration (for example, concentration by mass) of the compound (or compounds) in the same hydrocarbon mixture in the function F1, the polymerization temperature and the partial pressure PiC4 are measured;

(d) from the second and third measurements of the preceding step, the functions F1 and F2 are calculated;

(e) from F1, F2, CiC4 and the partial pressure measurement PiC4, a corrected partial pressure of PiC4, namely (PiC4)c, is calculated which is independent of any variations of CiC4, of the concentration (for example, concentration by mass) of the compound (or compounds) in the C4 hydrocarbon feed mixture in the function F1, or of the polymerization temperature, (f) the regulator compares a corrected value for the isobutene partial pressure (PiC4)c with the limits of the range as determined in (b);

(g) if the corrected value for the isobutene partial pressure (PiC4)c is within the limits of the range as determined in (b), the regulator is deactivated and the flow rates Qc and/or Qh remain unchanged;

(h) if the corrected value for the isobutene partial pressure (PiC4)c is outside the limits of the range as determined in (b):

(i) the value to be displayed as set point C of a regulator of the isobutene partial pressure in the gas phase of the reactor is calculated, in order to attain the target value V calculated in step (a), by varying the said set point C iteratively according to, preferably, a linear variation as a function of time and with a predetermined rate as mentioned above;

(ii) the regulator compares the corrected value (PiC4)c for the isobutene partial pressure with the set point C of the regulator, and calculates the difference E=C−(PiC4)c between these two values;

(iii) as a function of the difference E, the regulator acts on the flow rates Qc and/or Qh so as to shift the corrected isobutene partial pressure (PiC4)c towards the set point C. In particular, if the regulator acts on the flow rate Qc, alternatively the difference E is negative or less than the negative limit of a predetermined range centered around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged. Furthermore, if the regulator acts on the flow rate Qh, then the actions on the flow rate Qh are carried out, with respect to the difference E, in a manner which is exactly the opposite of those described above on the flow rate Qc: therefore, the flow rate Qh is reduced instead of than being increased, and vice versa.

One variant of the above forms of the process can consist in the regulator acting simultaneously on the flow rate Qc and Qh. As described above, a calculated value for the corrected isobutene partial pressure (PiC4)c is compared with the set point C of the regulator and the difference E=C−(PiC4)c between these two values is calculated. As a function of the difference E, the regulator acts simultaneously on the flow rates Qh and Qc so as to shift the isobutene partial pressure in the gas phase of the reactor towards the set point C: alternatively, the difference E is negative or less than the negative limit of a predetermined range centered around zero, in which case the flow rate Qh is reduced and the flow rate Qc is increased; or the difference E is positive or greater than the positive limit of the said range, in which case the flow rate Qh is increased and the flow rate Qc is reduced; or the difference E is zero or is within the limits of the said range, in which case the flow rates Qh and Qc remain unchanged.

According to one of the preferred embodiments in the present invention, it is found to be more advantageous to keep the corrected partial pressure (PiC4)c constant around the target value V by acting solely on the flow rate Qc of the catalyst introduced.

One of the advantages of the present invention is to improve the stability of the polymerization reaction and to reduce the polydispersity, i.e. the breadth of the distribution of the molecular masses of the polyisobutene produced, and to do so whatever may be the slight fluctuations in the polymerization temperature or in the quality of the C4 hydrocarbon feed mixture.

Another advantage of the present invention is to be able to hold the polymerization temperature constant with another process control, independent of the process control according to the present invention that is used to maintain the viscosity or the average molecular weight of the polymer produced at a constant desired value.

Hence, by maintaining constant the polymerization temperature independently of the viscosity or the average molecular weight allows to obtain a polymer with a steady quality and with a constant unsaturated termination content.

FIG. 1 shows diagrammatically a process for producing polyisobutene by continuous polymerization of isobutene in a reactor (1) which essentially comprises a cylindrical part (2). The reactor comprises a boiling liquid reaction phase (3) and a gas phase (4) which is above and in equilibrium with the said liquid phase. The reactor is equipped with a feed pipe for a C4 hydrocarbon feed mixture (5) comprising the monomer, with a catalyst feed pipe (6) and, optionally, with a cocatalyst feed pipe (7), the said pipes emerging in the cylindrical part (2) containing the boiling liquid reaction phase (3). The bottom part of the reactor is equipped with a pipe (8) for withdrawing the boiling liquid reaction phase which leads towards a purification device (9) comprising, for example, at least one distillation column, which column is intended for isolating the polymer produced via a pipe (10). The top part of the reactor containing the gas phase (4) can be equipped with a line (11), for recycling the gas phase, on which line is mounted a condenser (12) which allows the gas phase exiting the reactor (1) to be cooled and condensed by means of a cooling fluid which circulates in a pipe (13), the resultant condensate being returned into the reactor (1). In the top part of the reactor containing the gas phase, a manometer (14) allows the total pressure in the reactor to be measured, a thermometer (16) allows the temperature in the reactor to be measured and an analyser (15), such as a gas chromatograph allows the concentration (for example, concentration by mass) of isobutene in the gas phase to be measured. On the C4 hydrocarbon feed mixture feed pipe (5), analysers (17) and (18) such as gas chromatographs allow the concentration (for example, concentration by mass) of isobutene and the concentration of at least one of the other compounds considered in the function F1 to be measured. These five instruments are connected to a centralized control unit (19) whose elements, such as regulators and calculation modules, are described diagrammatically in FIG. 2.

Figure 2:
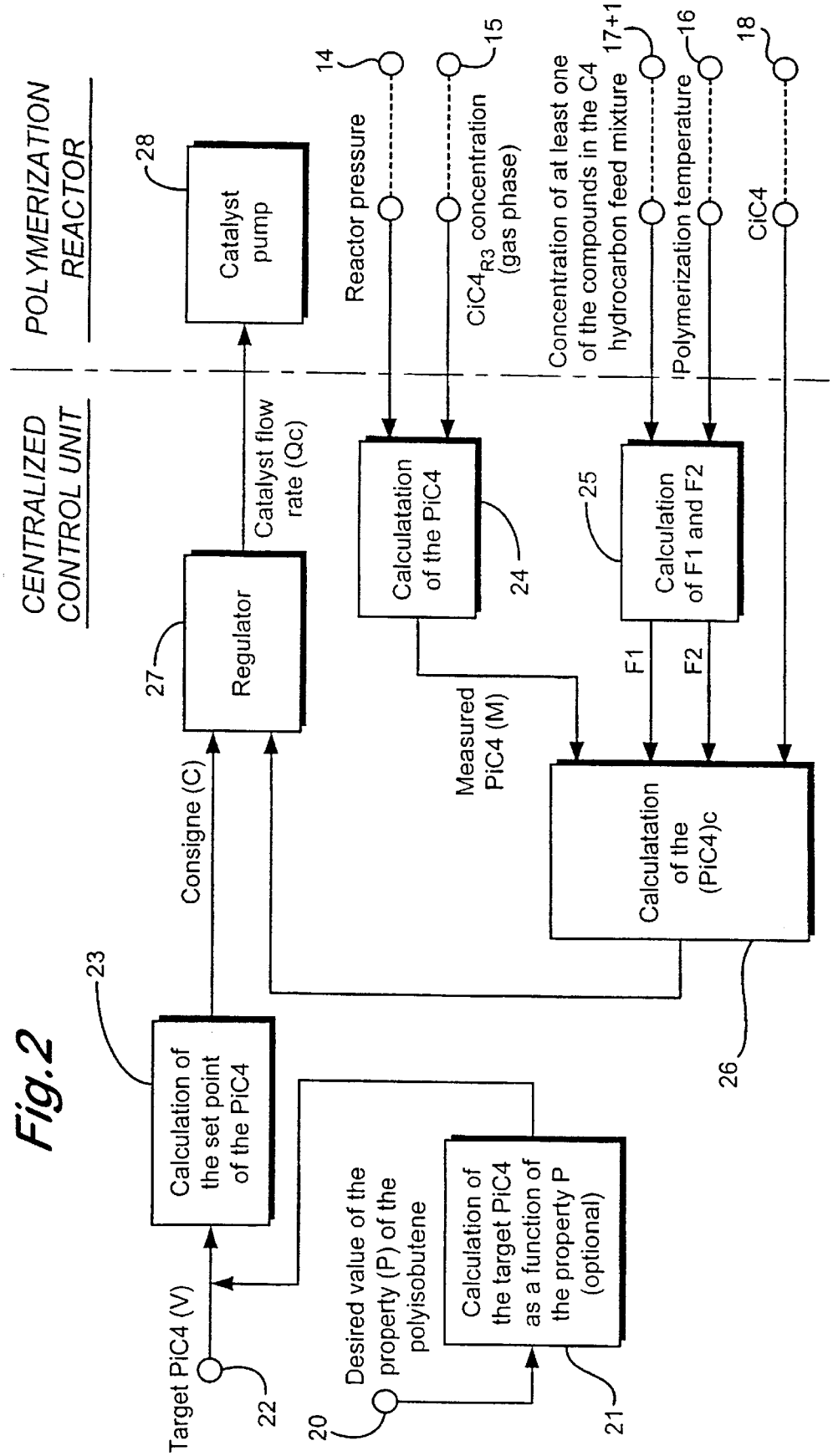
FIG. 2 shows, by way of example, a schematic diagram for controlling the property P of the polyisobutene produced continuously in accordance with the present invention.

FIG. 2 shows by way of example a schematic diagram of the process control according to the process of the present invention. For the elements described in the invention, this diagram shows on one side the instrumentation and equipment of the polymerization reactor (POLYMERIZATION REACTOR) and on the other side a functional schematic of the process control, which can be integrated into a centralized control unit (CENTRALIZED CONTROL UNIT).

According to FIG. 2, a calculation module (21) makes it possible to calculate the target value V for the isobutene partial pressure PiC4 in the gas phase of the reactor on the basis of the desired value (20) of the property P of the polyisobutene, by using an empirical relationship established beforehand between the property P of the polyisobutene produced and the partial pressure PiC4 of the isobutene in the gas phase of the reactor. The target value V (22) can, however, be calculated and entered directly by an operator into a calculation module (23). This module (23) makes it possible to calculate the set point C of the partial pressure PiC4 of the isobutene in the gas phase of the reactor on the basis of the target value V, by varying the said set point C iteratively over time. One Calculation module (25) makes it possible to calculate the functions F1 and F2 from the measurements of the concentration (for example, concentration by mass) of the compounds of the function F1 by the analysers (17) and (18) and of the polymerization temperature T measured by the thermometer (16). Another calculation module (24) is used to calculate the partial pressure PiC4 of the isobutene in the gas phase of the reactor on the basis of the measurement of the relative or absolute total pressure of the reactor, carried out for example using the manometer (14), and of the measurement of the concentration (for example, concentration by mass) of isobutene in the gas phase, carried out for example using the analyser (15), such as a gas chromatograph. The calculation module (26) makes it possible to calculate the corrected isobutene partial pressure (PiC4)c from the calculation of the functions F1 and F2, from the measurement of the concentration (for example, concentration by mass) of the isobutene by the analyser (18) and from the measured isobutene partial pressure M. The module (26) therefore yields a corrected value (PiC4)c which is transmitted to a regulator (27). This regulator (27):

(i) compares the corrected value (PiC4)c with the set point C calculated by the calculation module (23) and calculates the difference E=C−(PiC4)c between these two values;

(ii) as a function of the difference E, the regulator (27) acts, for example, on the flow rate Qc of catalyst delivered by a pump (28) in order to shift the corrected partial pressure (PiC4)c towards the set point C: alternatively, the difference E is negative or less than the negative limit of a predetermined range centered around zero, in which case the flow rate Qc of catalyst is increased; or the difference E is positive or greater than the positive limit of the said range, in which case the flow rate Qc of catalyst is reduced; or the difference E is zero or is within the limits of the said range, in which case the flow rate Qc of catalyst remains unchanged.

Figure 3:
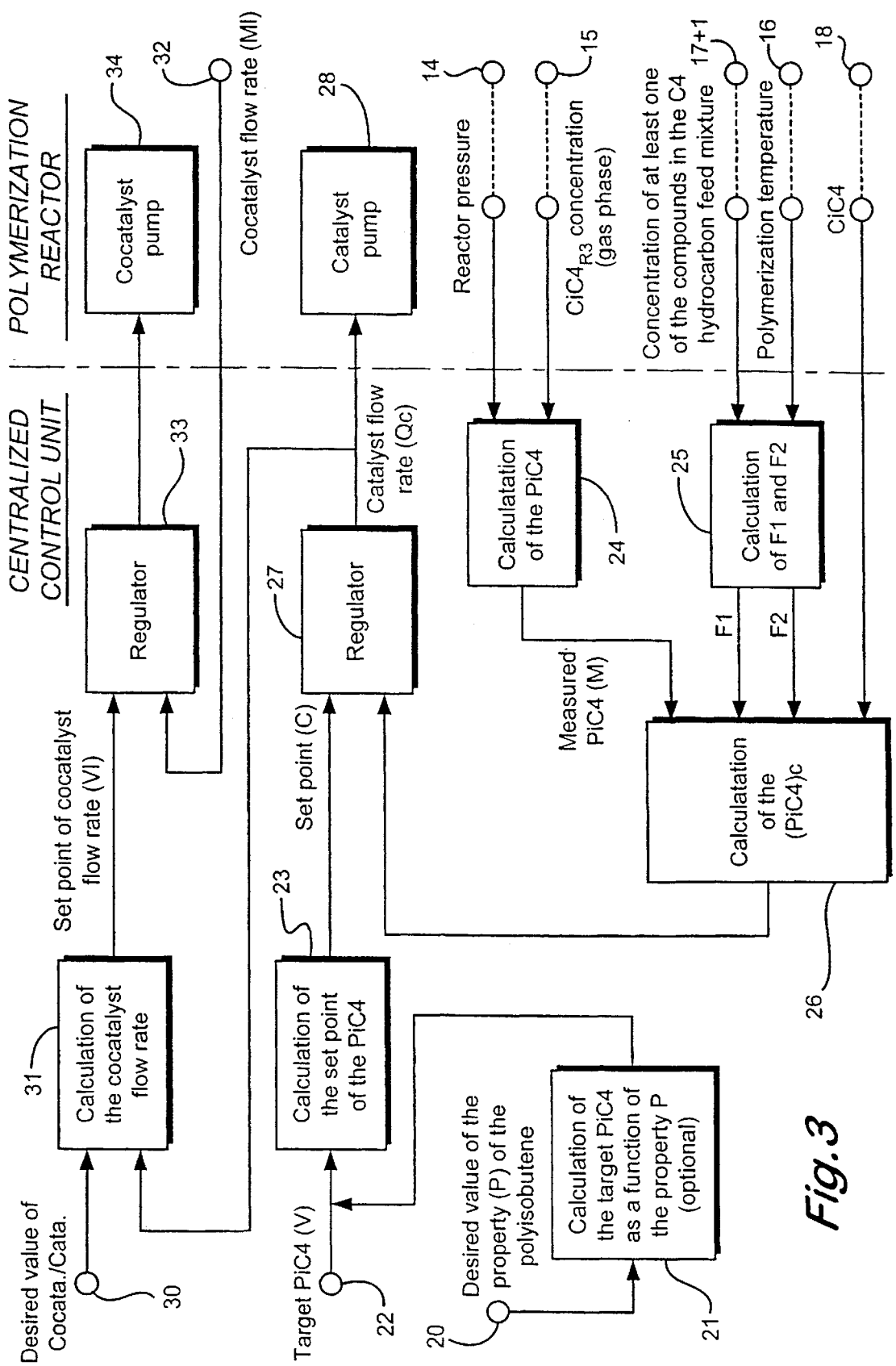
FIG. 3 shows, by way of example, a schematic diagram for controlling, which is improved relative to that shown in FIG. 2.

A preferred variant of the present invention is shown diagrammatically in FIG. 3, which in particular uses the elements labelled identically to those of FIG. 2. Furthermore, a catalyst and a cocatalyst are used simultaneously, the molar ratio of the amounts thereof introduced into the reactor being maintained at a constant desired value. Thus, in addition to the elements shown in FIG. 2, the diagram comprises a calculation module (31) which makes it possible, on the basis of the value for the flow rate of catalyst Qc calculated by the regulator (27), to calculate a desired value V1 for the flow rate of cocatalyst to be introduced into the reactor in order to maintain the molar ratio of the quantity of cocatalyst to the quantity of catalyst introduced at a constant desired value (30) which is entered by an operator into the calculation module (31). A regulator (33):

(i) compares a measured value M1 (32) for the flow rate of cocatalyst introduced into the reactor with the value V1 for the flow rate of cocatalyst calculated by the calculation module (31) and calculates the difference E1=V1−M1 between these two values;

(ii) as a function of the difference E1, the regulator (33) acts oh the flow rate of cocatalyst delivered by a pump (34) into the reactor in order to shift the flow rate of cocatalyst towards the desired value V1 calculated by the calculation module (31).

Figure 4B:
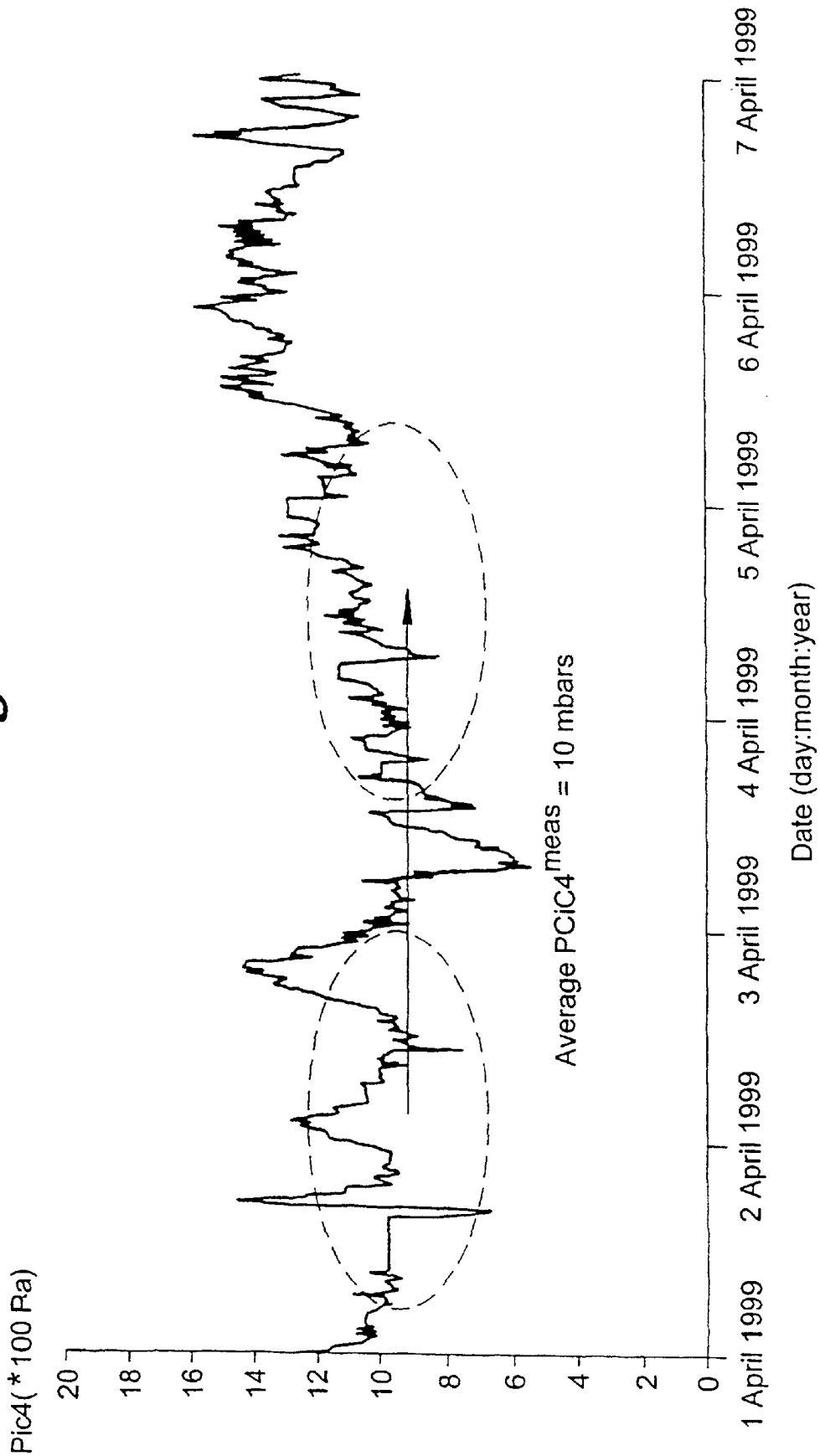
FIGS. 4.a, 4.b, 4.c show trends extracted from an episode of a polyisobutene production plant data illustrating the impact of a variation of the isobutane concentration in the C4 hydrocarbon feed mixture on the kinematic viscosity, when using a process control from the prior art.
Figure 4C:
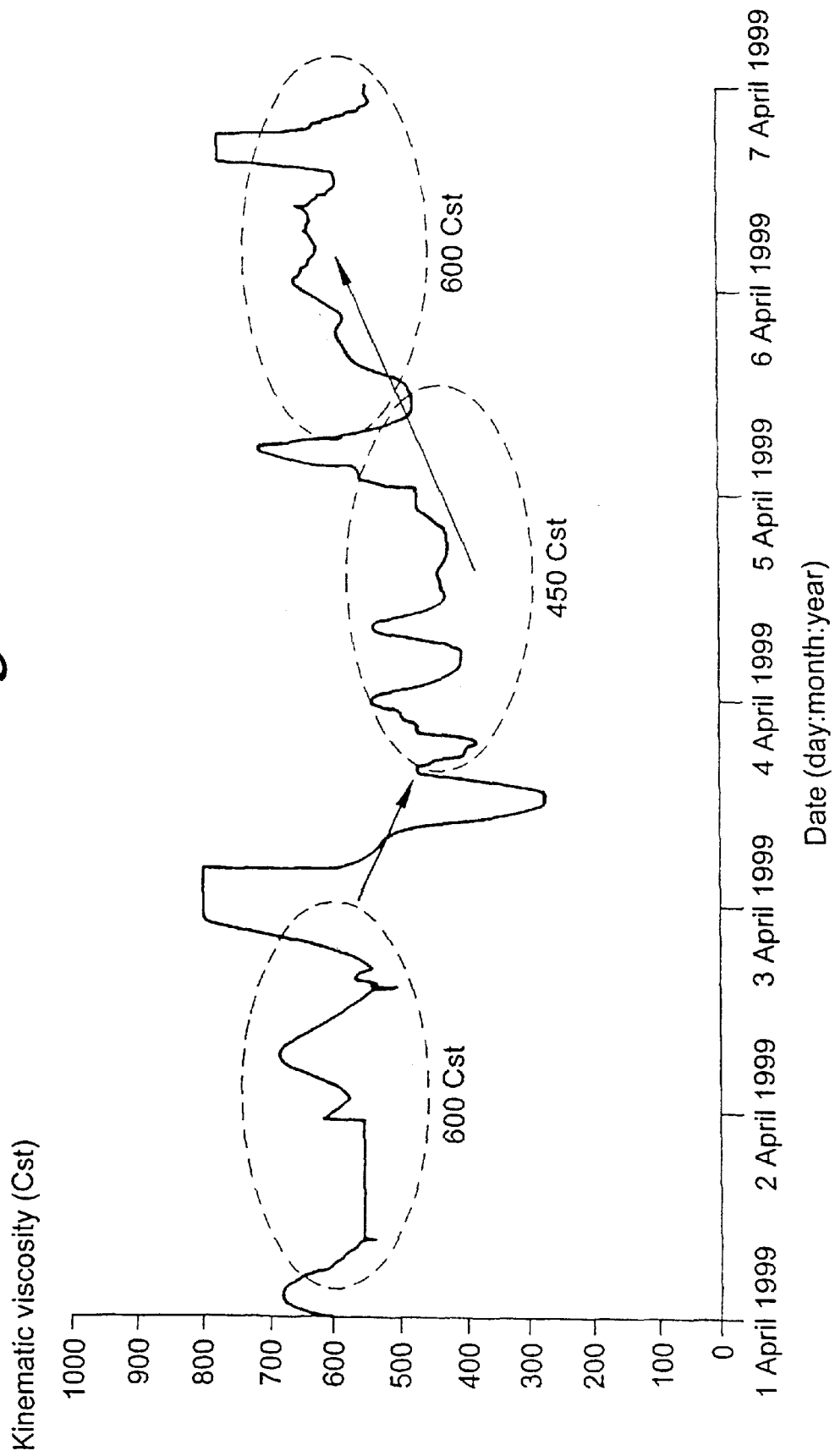

FIGS. 4.a, 4.b, 4.c show trends extracted from an episode of polyisobutene production plant data illustrating the impact of a variation of the isobutane concentration in the C4 hydrocarbon feed mixture on the kinematic viscosity, when using a process control from the prior art. The trends represented in FIGS. 4.a, 4.b and 4.c correspond to the variation as a function of time for a 6 days episode of respectively the isobutane concentration in the C4 hydrocarbon feed mixture, the partial pressure of isobutene, PiC4, measured in the gas phase of the reactor and the kinematic viscosity.

FIG. 5 represents a simulation showing on the same axis the measured and corrected value of the isobutene partial pressure, respectively (PiC4)*mes* and (PiC4)c , and shows the advantages of the present invention.

Figure 6B:
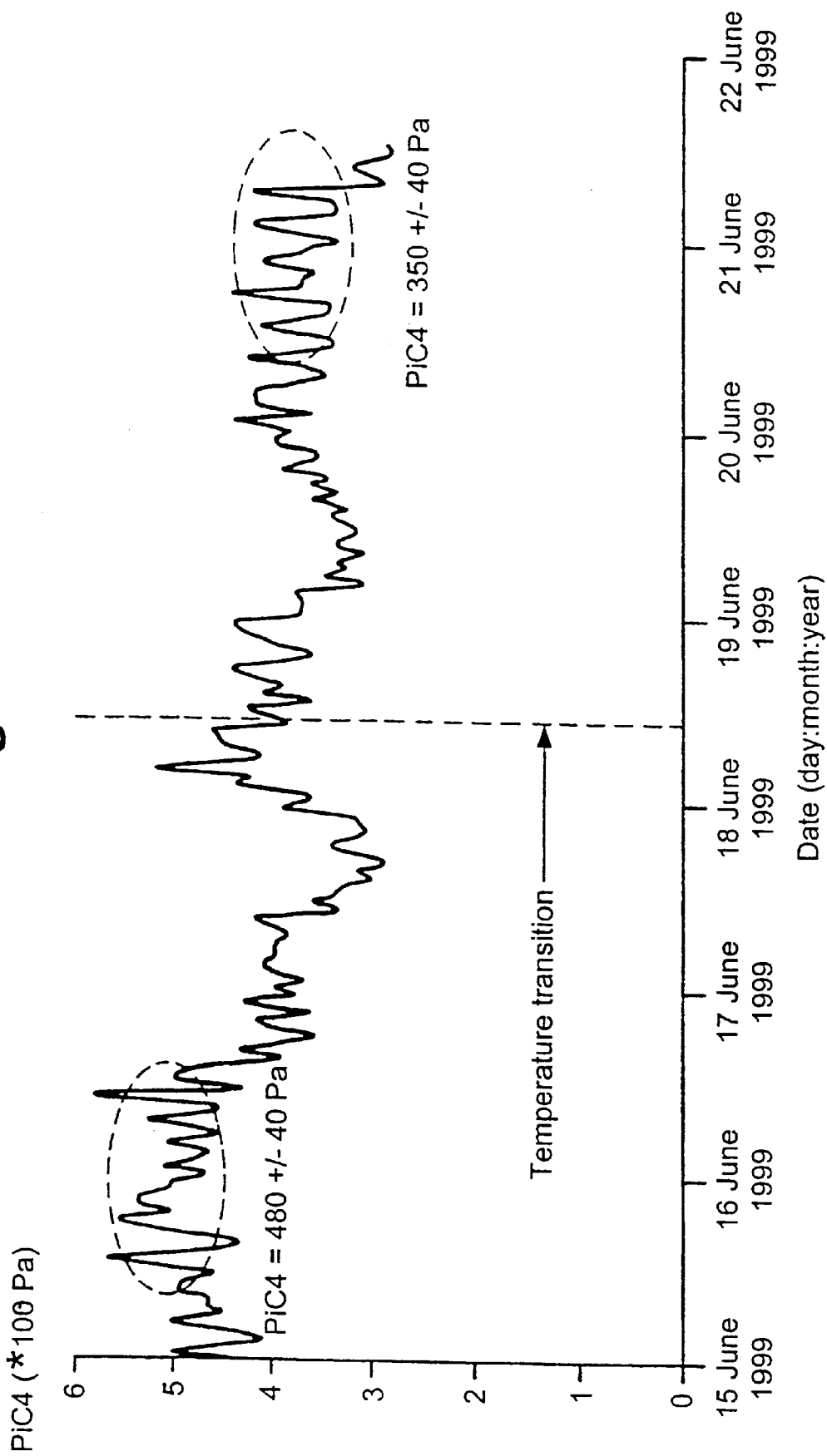
FIGS. 6.a, 6.b, 6.c show trends extracted from an episode of a polyisobutene production plant data illustrating the impact of a variation of the polymerization temperature on the kinematic viscosity, when using a process control from the prior art.

FIGS. 6.a, 6.b, 6.c show trends extracted from an episode of polyisobutene production plant data illustrating the impact of a variation of the polymerization temperature on the kinematic viscosity, when using a process control from the prior art. The trends represented in FIGS. 6.a, 6.b and 6.c correspond to the variation as a function of time for a 7 days episode of respectively the polymerization temperature, the partial pressure of isobutene, PiC4, measured in the gas phase of the reactor and the kinematic viscosity.

Figure 7:
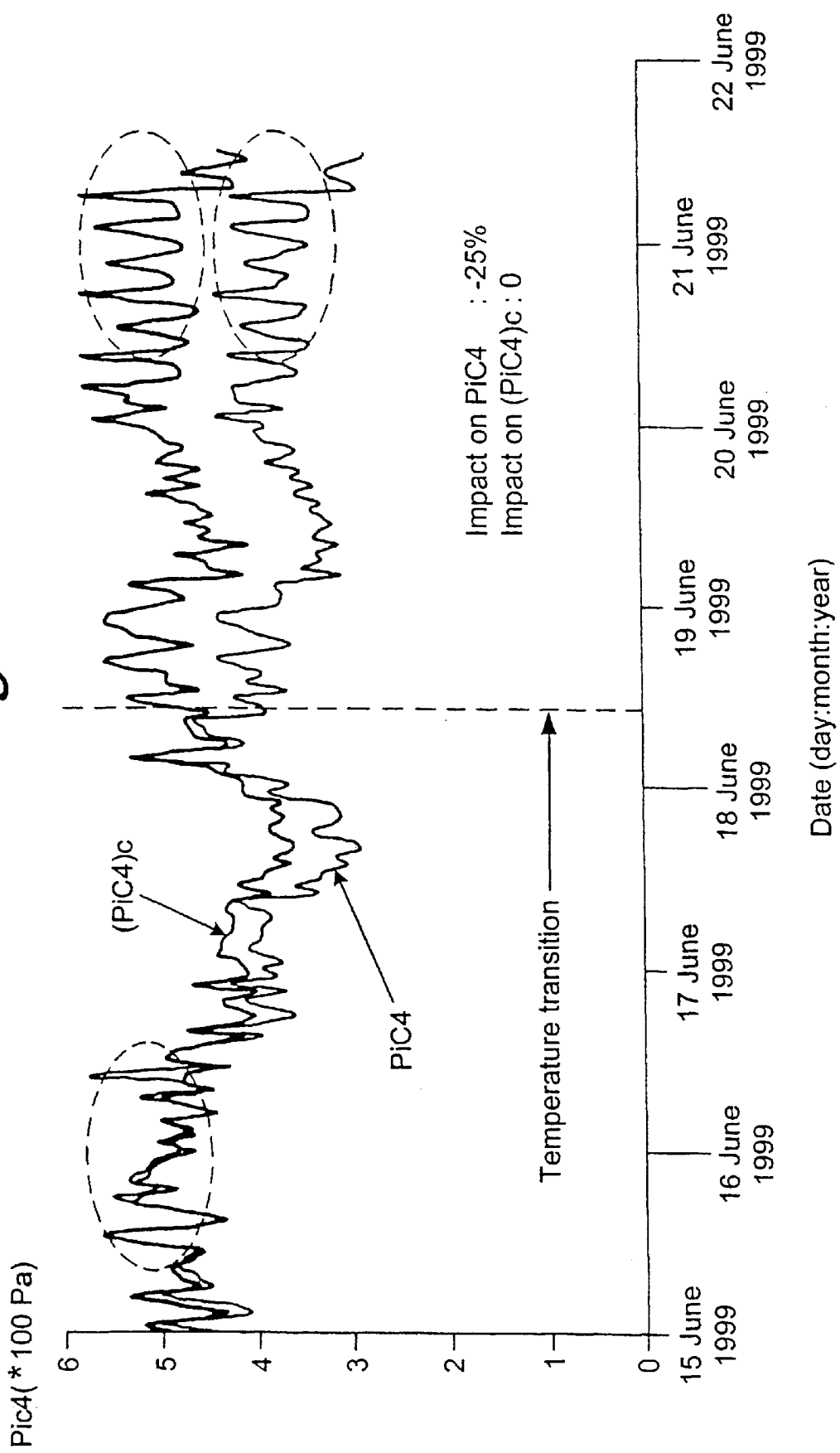
FIG. 7 represents a simulation showing on the same axis the measured and corrected value of the isobutene partial pressure for the same episode as previously, and shows the advantages of the present invention.

FIG. 7 represents a simulation showing on the same axis the measured and corrected value of the isobutene partial pressure, respectively (PiC4)*mes* and (PiC4)c , and shows the advantages of the present invention.

FIGS. 8.a, 8.b, 8.c show trends extracted from an episode of polyisobutene production plant data illustrating the impact of a variation of the C4 hydrocarbon feed mixture composition on the kinematic viscosity, when using a process control from the prior art. The trends represented in FIGS. 8.a, 8.b and 8.c correspond to the variation as a function of time for a 2 days episode of respectively the C4 hydrocarbon feed mixture composition, the partial pressure of isobutene, PiC4, measured in the gas phase of the reactor and the kinematic viscosity.

FIG. 9 represents a simulation showing on the same axis the measured and corrected value of the isobutene partial pressure, respectively (PiC4)*mes* and (PiC4)*c*, and shows the advantages of the present invention.

In the present description and in the present figures, the symbols will be understood as follows:

PiC4: Partial pressure of the isobutene in the gas phase of the reactor.
(PiC4)*c*: Corrected partial pressure of the isobutene in the gas phase of the reactor.
(PiC4)*m*: Modelled partial pressure of the isobutene in the gas phase of the reactor.
Qc: Flow rate (by mass) of catalyst.
Qh: Flow rate (by mass) of the C4 hydrocarbon feed mixture.
R2: Flow rate (by mass) of the polyisobutene produced.
R3: Flow rate (by mass) of the gas phase of the reactor which is recycled after cooling and condensation.
CiC4: Concentration (by mass) of the isobutene in the C4 hydrocarbon feed mixture.
$CiC4_{R2}$: Concentration (by mass) of the isobutene in the liquid phase of the reactor.
$CiC4_{R3}$: Concentration (by mass) of the isobutene in the gas phase of the reactor which is recycled after cooling and condensation.
Conv Rate of conversion of the isobutene to polymer.
Conv': Rate of conversion relative to the gas phase.
F1: Function of the concentration (by mass) of at least one of the compounds in the C4 hydrocarbon feed mixture.
F2: Function of the polymerization temperature.
a,A,B: Constants.
$K1, K2, k_{H0}$: Constants.
ki: Constant.
Ci: Concentration by mass of the compound i in the C4 hydrocarbon feed mixture.
$Ci_{av}$: Constant.
T: Polymerization temperature The following examples are based on trends extracted from three different episodes of the production plant data. The production plant was equipped with a process control of the prior art, wherein the isobutene partial pressure is held constant.

In the three episodes, the catalyst system included tert-butyl chloride as cocatalyst and ethyldichloroaluminium as catalyst. At the beginning of each episodes, the total flow rate of the liquid C4 hydrocarbon feed mixture was approximately around 15 T/h, the polymerization temperature was approximately 10° C. (except in the comparative example 5 and example 6), the reactor was fed continuously with a C4 hydrocarbon feed mixture through the conduit (5) containing approximately by weight, 8.5% of 1-butene, 12.7% of cis 2-butene, 22.3% of trans 2-butene, 45.7% of isobutene and 10.8% of butanes (except in the comparative example 3 and example 4).

COMPARATIVE EXAMPLE 1

This example is based on trends extracted from a production plant data, said plant being equipped with a process control of the prior art, wherein the isobutene partial pressure is held constant. The catalyst and the cocatalyst were introduced continuously through the feed pipes at a rate, in moles per tonne of C4 hydrocarbon feed mixture, respectively equal to 0.57 and 2.95 moles/tonne. The kinematic viscosity target was approximately 600 Cst. FIG. 4.*c* shows a drift of the average PIB viscosity from 600 Cst down to 450 Cst that was caused by an increase of the isobutane concentration in the C4 hydrocarbon feed mixture introduced into the reactor, as shown in FIG. 4.*a*. This event took place between Apr. 2nd 1999 and Apr. 4th 1999, in spites of maintaining the average isobutene partial pressure constant approximately around 1000 Pa, as shown in FIG. 4.*b*. In order to bring the viscosity back to its targeted value of 600 Cst, the isobutene partial pressure was increased from 1000 to 1300 Pa between Apr. 4th 1999 and Apr. 7th 1999, as shown in FIG. 4.*b*. It is clear from this example that a process control based on maintaining the isobutene partial pressure constant is not entirely satisfactory.

EXAMPLE 2

This example is based on a simulation using the same trends as for the comparative example 1. The isobutene partial pressure value was corrected according to the present invention and the corresponding trend was drawn on the same axis than the measured isobutene partial pressure PiC4 (not corrected) trend, as shown in FIG. 5. The corrected value of the isobutene pressure, (PiC4)*c*, was calculated from the measured value of PiC4, the polymerization temperature and the concentration of n-butane, isobutane, isobutene, 1-butene, 2cis butene, 2trans butene in the C4 hydrocarbon feed mixture. The corrected value (PiC4)*c* was significantly less affected by the variation of the isobutene concentration in the C4 hydrocarbon feed mixture in comparison to measured value of PiC4. The measured value PiC4 drifted by +30% between around Apr. 2nd 1999 (when the viscosity was around 600 Cst) and around Apr. 6th 1999 (when the viscosity was brought back to around 600 Cst after a drift down to 450 Cst). This confirms that a process control based only on maintaining the isobutene partial pressure constant is not entirely satisfactory. By comparison, the corrected value (PiC4)*c* only drifted by −10%. Hence a process control based on maintaining constant the corrected value of the isobutene partial pressure brings more benefit to the steadiness of the process.

COMPARATIVE EXAMPLE 3

As for the comparative example 1, this example is based on trends extracted from production plant data, the plant being equipped with the same process control of the prior art based on maintaining constant the isobutene partial pressure. The catalyst and the cocatalyst were introduced continuously through the feed pipes at a rate, in moles per tonne of C4 hydrocarbon feed mixture, respectively equal to 0.63 and 3.18 moles/tonne. The kinematic viscosity target was approximately equal to 250 Cst. FIG. 6.*c* shows two periods (Jun. 16th 1999 and Jun. 21st 1999) where the average PIB viscosity was maintained constant around the targeted value of 250 Cst Between these two periods, the viscosity was very difficult to control and the polymerization temperature was reduced from 11 to 10° C. on Jun. 18th 1999, as shown in FIG. 6.*a*. In order to bring the viscosity back to its targeted value of 250 Cst, the isobutene partial pressure was reduced from 480 to 350 Pa between around Jun. 16th 1999 and around Jun. 21st 1999, as shown in FIG. 6.*b*. It is clear from this example that a process control based on maintaining the isobutene partial pressure constant is not entirely satisfactory.

EXAMPLE 4

This example is based on a simulation using the same trends as for the comparative example 3. The isobutene partial pressure value was corrected according to the present invention and the corresponding trend was drawn on the same axis than the measured isobutene partial pressure PiC4 (not corrected) trend, as shown in FIG. 7. The corrected value of the isobutene pressure, (PiC4)c, was calculated using the same calculation as for Example 2. The corrected value (PiC4)c was significantly less affected by the variation of the polymerization temperature in comparison to the measured value of PiC4. The measured value PiC4 drifted by −25% between around Jun. 16th 1999 (when the viscosity was around 250 Cst) and Jun. 21st 1999 (when the viscosity was brought back to 250 Cst after important perturbations). This confirms again that a process control based only on maintaining the isobutene partial pressure constant is not entirely satisfactory. By comparison, the corrected value (PiC4)c hardly drifted. Hence a process control based on maintaining constant the corrected value of the isobutene partial pressure improves significantly the steadiness of the process.

COMPARATIVE EXAMPLE 5

As for the comparative example 1 and 3, this example is based on trends extracted from production plant data, the plant being equipped with the same process control of the prior art based on maintaining constant the isobutene partial pressure. The catalyst and the cocatalyst were introduced continuously through the feed pipes at a rate, in moles per tonne of C4 hydrocarbon feed mixture, respectively equal to 0.46 and 2.4 moles/tonne. The kinematic viscosity target was approximately 2800 Cst. FIG. 8.c shows two periods, at around Jul. 5th 1999 5:00 and at around Jul. 6th 1999 19:00, where the average PIB viscosity was maintained at around the targeted value of 2800 Cst. Between these two periods, the viscosity was very difficult to control and the composition of the C4 hydrocarbon feed mixture introduced into the reactor was significantly modified at around Jul. 6th 1999 1:00, as shown in FIG. 8.a. In order to bring the viscosity back to its targeted value of 2800 Cst, the isobutene partial pressure was reduced from 2400 to 1400 Pa between Jul. 5th 1999 5:00 and 6th Jul. 1999 19:00, as shown in FIG. 8.b. It is clear from this example that a process control based on maintaining the isobutene partial pressure constant is not entirely satisfactory.

EXAMPLE 6

This example is based on a simulation using the same trends as for the comparative example 5. The isobutene partial pressure value was corrected according to the present invention and the corresponding trend was drawn on the same axis than the measured isobutene partial pressure PiC4 (not corrected) trend, as shown in FIG. 9. The corrected value of the isobutene pressure, (PiC4)c, was calculated using the same calculation as for Example 4. The corrected value (PiC4)c was significantly less affected by the variation of the polymerization temperature in comparison to the measured value of PiC4. The measured value PiC4 drifted by −30% between Jul. 5th 1999 5:00 (when the viscosity was around 2800 Cst) and Jul. 6th 1999 19:00 (when the viscosity was brought back to 2800 Cst after important perturbatrons) This confirms again that a process control based only on maintaining the isobutene partial pressure constant is not entirely satisfactory. By comparison, the corrected value (PiC4)c hardly drifted. Hence a process control based on maintaining constant the corrected value of the isobutene partial pressure improves significantly the steadiness of the process.

What is claimed is:

1. Process for maintaining a property P of a polyisobutene at a constant desired value in the course of an isobutene polymerization conducted continuously in a reactor comprising a boiling liquid reaction phase which contains the monomer and the polymer being formed and is in equilibrium with a gas phase on top of the said liquid phase, said process comprising:
    conducting the polymerization by continuous introduction into the reactor of a catalyst and of a C4 hydrocarbon feed mixture comprising the monomer;
    continuously withdrawing the liquid reaction phase from the reactor; and
    subjecting the liquid reaction phase continuously to at least one purification step which is intended to isolate the polyisobutene produced,
    wherein the property P is selected from the viscosity and the average molecular mass of the polyisobutene produced,
    wherein a target value V is determined for the partial pressure PiC4 of the isobutene in the gas phase of the reactor, corresponding to the desired value of the property P by virtue of an empirical relationship between P and PiC4 established beforehand under polymerization conditions in the reactor, and
    wherein during the polymerization, the partial pressure PiC4 and at least one of the parameters selected from the polymerization temperature and the concentration of at least one of the constituents of the C4 hydrocarbon feed mixture are measured, a corrected value of the isobutene partial pressure, (PiC4)c, is calculated from the measured value of PiC4 and from that of at least one of the said parameters so that the corrected value (PiC4)c is an independent function of the parameters influencing the liquid/vapor equilibrium in the reactor, and the said corrected value (PiC4)c is held constant at said target value V by varying the flow rate Qc of the catalyst introduced into the reactor and/or the flow rate Qh of the C4 hydrocarbon feed mixture introduced into the reactor.

2. Process according to claim 1, wherein the partial pressure PiC4 is modeled as a function of the concentration of isobutene, CiC4, in the C4 hydrocarbon feed mixture, of a function F1 of the concentration of at least one compound in said feed mixture, of a function F2 of the polymerization temperature, of a function of the rate of conversion of the isobutene to polymer, and wherein:
    1) the concentration of isobutene, CiC4, in the C4 hydrocarbon feed mixture, the concentration of the compound (or compounds) in said feed mixture, the polymerization temperature and the partial pressure PiC4 are measured,
    2) from the measurements of the concentration of the compound(s) in said feed mixture and of the polymerization temperature carried out in step (1), the functions F1 and F2 are calculated,
    3) from F1, F2, CiC4 and the partial pressure measurement PiC4, a corrected partial pressure of PiC4, namely (PiC4)c, is calculated which is independent of any variations of CiC4, of the concentration of the compound (or compounds) in the C4 hydrocarbon feed mixture in the function F1, or of the polymerization temperature,
    4) the corrected partial pressure (PiC4)c is held constant at the target value, V, of PiC4 by varying the flow rates Qc and/or Qh.

3. Process according to claim wherein the property P is selected from the kinematic viscosity, the specific viscosity, the reduced viscosity and the intrinsic viscosity of the polyisobutene produced.

4. Process according to claim 1, wherein the property P is selected from the number-average molecular mass Mn or weight-average molecular mass Mw or viscometric average molecular mass Mv of the polyisobutene produced.

5. Process according to claim 1, wherein a catalyst is used which is suitable for cationic polymerization in the presence of a cocatalyst and wherein the molar ratio of the amount of cocatalyst to the amount of catalyst which are introduced into the reactor is held at a constant value.

6. Process according to claim 5, wherein the molar ratio of the amount of cocatalyst to the amount of catalyst which are introduced into the reactor is between 0.05 and 20.

7. Process according to claim 6, wherein the molar ratio of the amount of cocatalyst to the amount of catalyst which are introduced into the reactor is between 1 and 10.

8. Process according to claim 1, wherein the partial pressure PiC4 is modelled as a function of the concentration of isobutene, CiC4, in the C4 hydrocarbon feed mixture, of a function F1 of the concentration of at least one compound of the said feed mixture, of a function F2 of the polymerization temperature, of a function of the rate of conversion of the isobutene to polymer, and wherein:
   (a) the desired value of the property P is selected, and the target value V of the isobutene partial pressure in the gas phase of the reactor, corresponding to the desired value of the property P, is calculated with the aid of said empirical relationship;
   (b) the target value V calculated in step (a) is displayed as the set point of a regulator of the corrected isobutene partial pressure;
   (c) the concentration of isobutene, CiC4, in the C4 hydrocarbon feed mixture, the concentration of the compound (or compounds) in said feed mixture, the polymerization temperature and the partial pressure PiC4 are measured;
   (d) from the measurements of the concentration of the compound(s) in said feed mixture and of the polymerization temperature carried out in step (c), the functions F1 and F2 are calculated;
   (e) from F1, F2, CiC4 and the partial pressure measurement PiC4, a corrected partial pressure of PiC4, namely (PiC4)$c$, is calculated which is independent of any variations of CiC4, of the concentration of the compound(s) in said feed mixture, or of the polymerization temperature;
   (f) the regulator compares the corrected value for the isobutene partial pressure (PiC4)$c$ with the target value V calculated in step (a) and calculates the difference E=V−(PiC4)$c$ between these two values;
   (g) as a function of the difference E calculated in step (f), the regulator varies the flow rates Qc and/or Qh so as to shift the isobutene partial pressure in the gas phase of the reactor towards the target value V.

9. Process according to claim 1, wherein the partial pressure PiC4 is modelled as a function of the concentration of isobutene, CiC4, in the C4 hydrocarbon feed mixture, of a function F1 of the concentration of at least one compound of the said feed mixture, of a function F2 of the polymerization temperature, of a function of the rate of conversion of the isobutene to polymer, and wherein the process comprises the following steps:
   (a) the desired value of the property P is selected, and the target value V of PiC4, corresponding to the desired value of the property P, is calculated with the aid of said empirical relationship;
   (b) the value to be displayed as set point C of a regulator of the corrected isobutene partial pressure, in order to reach the target value V calculated in step (a), is calculated by an iterative variation as a function of time of said set point C;
   (c) the concentration of isobutene, CiC4, in the C4 hydrocarbon feed mixture, the concentration of the compound(s) in said feed mixture, the polymerization temperature and the partial pressure PiC4 are measured;
   (d) from the measurements of the concentration of the compound(s) in said feed mixture and of the polymerization temperature carried out in step (c), the functions F1 and F2 are calculated;
   (e) from F1, F2, CiC4 and the partial pressure measurement PiC4, a corrected partial pressure of PiC4, namely (PiC4)$c$, is calculated which is independent of any variations of CiC4, of the concentration of the compound(s) in said feed mixture, or of the polymerization temperatures;
   (f) the regulator compares a corrected value for the isobutene partial pressure (PiC4)$c$ with the set point C of the regulator calculated in step (b) and calculates the difference E=C−(PiC4)$c$ between these two values;
   (g) as a function of the difference E calculated in step (f), the regulator varies the flow rates Qc and/or Qh so as to shift the isobutene partial pressure in the gas phase of the reactor towards the set point C.

10. Process according to claim 9, wherein the target value V of the corrected partial pressure (PiC4)$c$ is reached by an iterative variation, which is linear as a function of time, of the said corrected partial pressure (PiC4)$c$ of isobutene with a rate varying from 100 to 2000 Pa/h.

11. Process according to claim 10, wherein the rate varies from 500 to 1500 Pa/h.

12. Process according to claim 1, wherein the partial pressure PiC4 is modelled as a function of the concentration of isobutene, CiC4, in the C4 hydrocarbon feed mixture, of a function F1 of the concentration of at least one compound of the said feed mixture, of a function F2 of the polymerization temperature, of a function of the rate of conversion of the isobutene to polymer, and wherein the process comprises the following steps:
   (a) the desired value of the property P is selected, and the target value V of PiC4, corresponding to the desired value of the property P, is calculated with the aid of said empirical relationship;
   (b) the target value V calculated in step (a) is displayed as set point C of a regulator of the corrected isobutene partial pressure;
   (c) the limits of a range of values for the corrected isobutene partial pressure (PiC4)$c$ in the gas phase of the reactor are determined in a range around the target value V with limits not being more than ±20%;
   (d) the concentration of isobutene, CiC4, in the C4 hydrocarbon feed mixture, the concentration of the compound(s) in said feed mixture, the polymerization temperature and the partial pressure PiC4 are measured;
   (e) from the measurements of the concentration of the compound(s) in said feed mixture and of the polymerization temperature carried out in step (d), the functions F1 and F2 are calculated;

(f) from F1, F2, CiC4 and the partial pressure measurement PiC4, a corrected partial pressure of PiC4, namely (PiC4)$c$, is calculated which is independent of any variations of CiC4, of the concentration of the compound(s) in said feed mixture, or of the polymerization temperature;

(g) the regulator compares the corrected value for the isobutene partial pressure (PiC4)$c$ with the said limits of the range as determined in step (c);

(h) if the corrected value (PiC4)$c$ for the isobutene partial pressure is within the limits of the range as determined in step (c), the regulator is deactivated and the flow rates Qc and/or Qh remain unchanged;

(i) if the corrected value (PiC4)$c$ for the isobutene partial pressure is outside the limits of the range as determined in step (c):

(i) the regulator compares the corrected value (PiC4)$c$ for the isobutene partial pressure in the gas phase of the reactor with the set point C of the regulator, and calculates the difference E=C−(PiC4)$c$ between these two values;

(ii) as a function of the difference E, the regulator varies on the flow rates Qc and/or Qh so as to shift the corrected (PiC4)$c$ isobutene partial pressure towards the set point C.

13. Process according to claim 12, wherein the predetermined range around the target value V is not more than ±10% around V.

* * * * *